US011464658B2

(12) United States Patent
Kawwas et al.

(10) Patent No.: US 11,464,658 B2
(45) Date of Patent: Oct. 11, 2022

(54) IMPLANTABLE MEDICAL DEVICE WITH CAVITATION FEATURES

(71) Applicant: Medtronic Vascular, Inc., Santa Rosa, CA (US)

(72) Inventors: Jaclyn Kawwas, San Francisco, CA (US); Radhika Bhargav, Mountain View, CA (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 440 days.

(21) Appl. No.: 16/657,595

(22) Filed: Oct. 18, 2019

(65) Prior Publication Data

US 2020/0129316 A1 Apr. 30, 2020

Related U.S. Application Data

(60) Provisional application No. 62/750,537, filed on Oct. 25, 2018.

(51) Int. Cl.

| | |
|---|---|
| ***A61F 2/93*** | (2013.01) |
| ***A61F 2/24*** | (2006.01) |
| ***A61F 2/86*** | (2013.01) |
| ***A61N 1/362*** | (2006.01) |
| ***A61N 1/05*** | (2006.01) |

(52) U.S. Cl.

CPC .............. *A61F 2/93* (2013.01); *A61F 2/2433* (2013.01); *A61F 2/86* (2013.01); *A61N 1/05* (2013.01); *A61N 1/362* (2013.01)

(58) Field of Classification Search

CPC ........ A61B 17/22004; A61B 17/22012; A61B 17/22029; A61B 2017/22005; A61B 2017/22027; A61F 2/93; A61F 2/2433; A61F 2/86; A61N 1/05; A61N 1/362

See application file for complete search history.

(56) References Cited

U.S. PATENT DOCUMENTS

| | | | |
|---|---|---|---|
| 8,574,247 | B2 | 11/2013 | Adams et al. |
| 9,011,463 | B2 | 4/2015 | Adams et al. |
| 9,044,618 | B2 | 6/2015 | Hawkins et al. |
| 9,220,521 | B2 | 12/2015 | Hawkins et al. |

(Continued)

FOREIGN PATENT DOCUMENTS

| | | | |
|---|---|---|---|
| CN | 107261301 | A | 10/2017 |
| EP | 1415616 | A1 | 5/2004 |

(Continued)

OTHER PUBLICATIONS

PCT/US2019/057259, The International Search Report and Written Opinion, dated Mar. 24, 2020, 17pgs.

(Continued)

*Primary Examiner* — Thomas McEvoy

(57) ABSTRACT

In some examples, the disclosure describes a medical assembly that includes a stent including a primary electrode, where the stent is configured to expand from a collapsed configuration to an expanded configuration, a secondary electrode, and an energy source configured to deliver an electrical signal between the primary electrode and the secondary electrode through a fluid in contact with the primary electrode to cause the fluid to undergo cavitation to generate a pressure pulse wave within the fluid.

20 Claims, 14 Drawing Sheets

22B 70 42 40 62 46A 22A 66 68 32B 45 26 60 46B 64 42B 22 24

(56) References Cited

U.S. PATENT DOCUMENTS

| | | | | |
|---|---|---|---|---|
| 9,554,815 | B2 | 1/2017 | Adams | |
| 9,717,513 | B2 | 8/2017 | Golan | |
| 9,730,715 | B2 | 8/2017 | Adams | |
| 2009/0143777 | A1* | 6/2009 | Pacey | A61B 18/1492 607/113 |
| 2011/0264039 | A1 | 10/2011 | Thielen et al. | |
| 2012/0109179 | A1 | 5/2012 | Murphy et al. | |
| 2014/0025087 | A1 | 1/2014 | Richardson | |
| 2016/0184570 | A1 | 6/2016 | Grace et al. | |
| 2016/0262784 | A1* | 9/2016 | Grace | A61B 17/22022 |
| 2017/0333451 | A1* | 11/2017 | Hoffman | A61P 1/18 |
| 2018/0126127 | A1 | 5/2018 | Devereux et al. | |
| 2018/0133443 | A1 | 5/2018 | Osypka | |
| 2018/0153692 | A1 | 6/2018 | Gerhardt et al. | |
| 2019/0262594 | A1* | 8/2019 | Ogata | A61N 1/306 |

FOREIGN PATENT DOCUMENTS

| | | | |
|---|---|---|---|
| WO | 2017070252 | A1 | 4/2017 |
| WO | 2018075924 | A1 | 4/2018 |

OTHER PUBLICATIONS

PCT/US2019/057249, The International Search Report and the Written Opinion, dated Mar. 12, 2020, 18pgs.

* cited by examiner

IMPLANTABLE MEDICAL DEVICE WITH CAVITATION FEATURES

CROSS REFERENCE TO RELATED APPLICATIONS

This Non-Provisional Patent Application claims the benefit of the filing date of U.S. Provisional Patent Application Ser. No. 62/750,537, filed Oct. 25, 2018, entitled “Cavitation Stent,” which is herein incorporated by reference.

TECHNICAL FIELD

This disclosure relates to medical stents and medical assemblies for introducing stents into the body of a patient.

BACKGROUND

Patient conditions associated with heart valves such as, but not limited to, calcification, can produce a stenosis and/or valvular insufficiency or regurgitation. Valvular insufficiency or regurgitation occurs when a valve in a heart of a subject does not close completely, allowing blood to flow backwards (e.g., from the left ventricle to the left atrium), which may adversely impact the functionality of the heart. In some cases, valvular stenosis can cause the valve to become narrowed and hardened, which may prevent the valve from opening fully, thereby reducing blood flow through the valve. This reduced blood flow may cause the heart to work harder to pump blood through the diseased valve.

Heart valve prostheses have been developed for repair and replacement of diseased and/or damaged heart valves. Some heart valve prostheses can be percutaneously delivered and deployed at the site of the diseased heart valve through a medical delivery system such as a catheter. An example of such a medical procedure is the transcatheter aortic valve replacement (TAVR) procedure. In some cases, a heart valve prostheses includes an expandable stent to which tissue defining valves are mounted. The heart valve prostheses can be delivered while the stent is in a low-profile or collapsed configuration so that the stent is in a low-profile state for advancement through the patient’s vasculature. Once positioned at the target treatment site, the stent can be expanded to engage native tissue at a target treatment site and position the heart valve prostheses at the target treatment site.

SUMMARY

In some aspects, this disclosure describes example medical assemblies that include a medical stent including one or more electrodes carried by the stent and electrically coupled to an energy source via one or more electrical conductors. The stent is configured to be implanted in cardiovasculature of a patient and can be, for example, part of a heart valve prostheses or a stent configured to be implanted in a blood vessel of a patient to help improve patency of the vessel. The energy source may be configured to deliver an electrical signal between the electrode carried by the stent and a second electrode through a fluid in contact with the electrode of the stent to cause the fluid to undergo cavitation to generate a pressure pulse wave within the fluid.

The cavitation of the fluid may be used treat a condition in a heart of a patient or in the vasculature of a patient. For example, the cavitation may produce a high-energy pressure pulse wave that, when directed at a valvular stenosis, may be used to disrupt and fracture calcification partially or fully causing the valvular stenosis. The disruption and fracture of the calcification may allow a heart valve prosthesis (also referred to herein as an artificial heart valve or a prosthetic heart valve) to be more easily and/or fully expanded in place in the heart. In examples in which the cavitation is used to disrupt and fracture calcification in a blood vessel of a patient, the disruption and fracture of the calcification may allow a stent to easily and/or fully expanded in the vessel, e.g., to achieve better patency of the vessel and achieve better blood flow through the vessel. In some other aspects, the disclosure describes methods of delivering and using the medical stents described herein.

Clause 1: In one example, a medical assembly includes a stent including a primary electrode, where the stent is configured to expand from a collapsed configuration to an expanded configuration, a secondary electrode, and an energy source configured to deliver an electrical signal between the primary electrode and the secondary electrode through a fluid in contact with the primary electrode to cause the fluid to undergo cavitation to generate a pressure pulse wave within the fluid.

Clause 2: In some of the examples of the medical assembly of clause 1, the medical assembly further including an electrical conductor having a distal end electrically coupled to the primary electrode and a proximal end electrically coupled to the energy source.

Clause 3: In some of the examples of the medical assembly of clause 1or 2, the stent includes a nickel-titanium alloy.

Clause 4: In some of the examples of the medical assembly of any one of clauses 1 to 3, the stent is configured to self-expand from the collapsed configuration to the expanded configuration.

Clause 5: In some of the examples of the medical assembly of any one of clauses 1 to 3, the medical assembly further including a balloon configured to expand the stent from the collapsed configuration to the expanded configuration.

Clause 6: In some of the examples of the medical assembly of any one of clauses 1 to 5, the stent includes a plurality of electrodes including the primary electrode.

Clause 7: In some of the examples of the medical assembly of any one of clauses 1 to 6, the stent includes a metallic body and a dielectric coating over a portion of the metallic body, a surface of the metallic body defining the primary electrode.

Clause 8: In some of the examples of the medical assembly of clause 7, the stent further includes an electrically conductive coating on the dielectric coating, where the dielectric coating prevents direct contact between the electrically conductive coating and the metallic body, the electrically conductive coating defining the secondary electrode.

Clause 9: In some of the examples of the medical assembly of clause 8, the electrically conductive coating and the dielectric coating define an electrode aperture that extends through a thickness of the electrically conductive coating and the dielectric coating, the electrode aperture exposing the surface of the metallic body to the fluid.

Clause 10: In some of the examples of the medical assembly of clause 7, further including a band of electrically conductive material that defines the secondary electrode, where the band is attached to the stent such that the dielectric coating prevents direct contact between the band and the metallic body.

Clause 11: In some of the examples of the medical assembly of any one of clauses 1 to 7, the medical assembly further including a guidewire defining the secondary electrode.

Clause 12: In some of the examples of the medical assembly of clause 11, where the guidewire is electrically coupled to the energy source.

Clause 13: In some of the examples of the medical assembly of any one of clauses 1 to 7, the medical assembly further including a catheter including an inner elongated member including the secondary electrode, and an outer elongated member configured to be retracted relative to the inner elongated member, in which the stent is configured to be positioned between the inner and outer elongated members, where when the outer elongated member is retracted relative to the inner elongated member such that a distal end of the outer elongated member is proximal to a distal end of the stent and distal to a proximal end of the stent, the distal end of the stent is configured to expand to a partially expanded configuration, and where the catheter and the stent are configured to deliver the electrical signal between the primary electrode and the secondary electrode while the stent is in the partially expanded configuration.

Clause 14: In some of the examples of the medical assembly of clause 13, the secondary electrode defines an exterior surface of a distal tip of the inner elongated member.

Clause 15: In some of the examples of the medical assembly of clause 13 or 14, the secondary electrode includes an electrically conductive ring positioned around the inner elongated member.

Clause 16: In some of the examples of the medical assembly of any one of clauses 13 to 15, the catheter further includes an electrical contact defining a surface of either the inner elongated member or the outer elongated member, where, while in the partially expanded configuration within the catheter, the stent contacts the electrical contact to electrically couple the primary electrode to the energy source.

Clause 17: In some of the examples of the medical assembly of clause 16, the electrical contact includes an electrically conductive ring positioned over the inner elongated member.

Clause 18: In some of the examples of the medical assembly of any one of clauses 13 to 16, where when the outer elongated member is retracted relative to the inner elongated member such that the distal end of the outer elongated member is proximal to the proximal end of the stent, the stent is configured to expand to the expanded configuration.

Clause 19: In some of the examples of the medical assembly of any one of clauses 13 to 17, the medical assembly further including a balloon attached to the inner elongated member, where the balloon is configured to expand the stent to the expanded configuration.

Clause 20: In some of the examples of the medical assembly of any one of clauses 1 to 19, the primary electrode is at a distal end of the stent.

Clause 21: In some of the examples of the medical assembly of any one of clauses 1 to 20, where the stent includes an artificial heart valve member.

Clause 22: In some of the examples of the medical assembly of any one of clauses 1 to 21, the stent is a transcatheter heart valve.

Clause 23: In some of the examples of the medical assembly of any one of clauses 1 to 22, the stent is configured to be implanted within a body of a patient.

Clause 24: In one example, a medical assembly includes a catheter including an inner elongated member including a secondary electrode, and an outer elongated member configured to be retracted relative to the inner elongated member, and a stent including a primary electrode, where the stent is configured to be positioned between the inner and outer elongated members, the stent being configured to expand from a collapsed configuration to an expanded configuration, where the secondary electrode and the primary electrode are configured to be electrically coupled to an energy source configured to deliver an electrical signal between the primary electrode and the secondary electrode through a fluid in contact with both the primary electrode and the secondary electrode to cause the fluid to undergo cavitation to generate a pressure pulse wave within the fluid.

Clause 25: In some of the examples of the medical assembly of clause 24, the medical assembly further including the energy source electrically coupled to the catheter, the energy source configured to deliver the electrical signal via the catheter to the primary electrode and the secondary electrode to cause the fluid to undergo cavitation.

Clause 26: In some of the examples of the medical assembly of clause 24 or 25, where the catheter further includes an electrical contact defining a surface of either the inner elongated member or the outer elongated member, where, while in the collapsed configuration within the catheter, the stent contacts the electrical contact to electrically couple the stent to the energy source.

Clause 27: In some of the examples of the medical assembly of clause 26, the stent includes a metallic body and a dielectric coating over a portion of the metallic body, a first surface of the metallic body defining the primary electrode, and a second surface of the metallic body in direct contact with the electrical contact while the stent is in the collapsed configuration.

Clause 28: In some of the examples of the medical assembly of clause 27, the metallic body includes a nickel-titanium alloy.

Clause 29: In some of the examples of the medical assembly of any one of clauses 24 to 28, the stent includes a plurality of electrodes including the primary electrode, each electrode of the plurality of electrodes positioned at the distal end of the stent.

Clause 30: In some of the examples of the medical assembly of any one of clauses 24 to 29, the secondary electrode defines an exterior surface of a distal tip of the inner elongated member.

Clause 31: In some of the examples of the medical assembly of any one of clauses 24 to 30, the secondary electrode includes an electrically conductive ring positioned over the inner elongated member.

Clause 32: In some of the examples of the medical assembly of any one of clauses 24 to 31, the electrical contact includes an electrically conductive ring positioned over the inner elongated member.

Clause 33: In some of the examples of the medical assembly of any one of clauses 24 to 32, where when the outer elongated member is retracted relative to the inner elongated member such that a distal end of the outer elongated member is proximal to a distal end of the stent and distal to a proximal end of the stent, the distal end of the stent is configured to expand to a partially expanded configuration, and where the catheter and the stent are configured to deliver the electrical signal between the primary electrode and the secondary electrode while the stent is in the partially expanded configuration.

Clause 34: In some of the examples of the medical assembly of any one of clauses 24 to 33, where when the outer elongated member is retracted relative to the inner elongated member such that the distal end of the outer elongated member is proximal to the proximal end of the stent, the stent is configured to expand to the expanded configuration.

Clause 35: In some of the examples of the medical assembly of any one of clauses 24 to 34, the medical assembly further including a balloon attached to the inner elongated member, the balloon configured to expand the stent to the expanded configuration.

Clause 36: In some of the examples of the medical assembly of any one of clauses 24 to 35, where the stent is configured to self-expand from the collapsed configuration to the expanded configuration.

Clause 37: In some of the examples of the medical assembly of any one of clauses 24 to 36, the stent includes an artificial heart valve member.

Clause 38: In some of the examples of the medical assembly of any one of clauses 24 to 37, the stent is a transcatheter heart valve.

Clause 39: In some of the examples of the medical assembly of any one of clauses 24 to 38, the stent is configured to be implanted within a body of a patient.

Clause 40: In one example, a medical stent includes a metallic body defining a primary electrode, a dielectric coating positioned over a portion of the metallic body, and a secondary electrode on the dielectric coating, where the dielectric coating prevents direct contact between the secondary electrode and the metallic body, where the secondary electrode and the primary electrode are configured to be electrically coupled to an energy source configured to deliver an electrical signal between the primary electrode and the secondary electrode through a fluid in contact with both the primary electrode and the secondary electrode to cause the fluid to undergo cavitation to generate a pressure pulse wave within the fluid.

Clause 41: In some of the examples of the medical stent of clause 40, the stent further includes an electrically conductive coating on the dielectric coating, where the dielectric coating prevents direct contact between the electrically conductive coating and the metallic body, the electrically conductive coating defining the secondary electrode.

Clause 42: In some of the examples of the medical stent of clause 41, the electrically conductive coating and the dielectric coating define an electrode aperture that extends through a thickness of the electrically conductive coating and the dielectric coating, the electrode aperture exposing the primary electrode to an external environment of the stent.

Clause 43: In some of the examples of the medical stent of clause 40, the medical stent further including a band of electrically conductive material that defines the secondary electrode, where the band is attached to the stent such that the dielectric coating prevents direct contact between the band and the metallic body.

Clause 44: In some of the examples of the medical stent of any one of clauses 40 to 43, the medical stent further including an artificial heart valve member.

Clause 45: In some of the examples of the medical stent of any one of clauses 40 to 44, the stent is a transcatheter heart valve.

Clause 46: In some of the examples of the medical stent of any one of clauses 40 to 45, the stent is configured to be implanted within a body of a patient.

Clause 47: In one example, a method includes coupling a stent to an energy source, where the stent includes primary electrode, the stent is configured to expand from a collapsed configuration to an expanded configuration; electrically coupling a secondary electrode to the energy source; and delivering, using the energy source, an electrical signal between the primary electrode and the secondary electrode through a fluid in contact with the primary electrode to cause the fluid to undergo cavitation to generate a pressure pulse wave within the fluid.

Clause 48: In some of the examples of the method of clause 47, the secondary electrode is carried by a catheter includes an inner elongated member including the secondary electrode, and an outer elongated member configured to be retracted relative to the inner elongated member, where the stent is configured to be positioned between the inner and outer elongated members. The method further includes retracting the outer elongated member relative to the inner elongated member such that a distal end of the outer elongated member is proximal to a distal end of the stent and distal to a proximal end of the stent, where retracting the outer elongated member includes expanding the distal end of the stent to a partially expanded configuration within the fluid, where while in the partially expanded configuration the primary electrode is configured to be electrically coupled to the energy source via the catheter, and where delivering the electrical signal between the primary electrode and the secondary electrode includes delivering the electrical signal while the stent is in the partially expanded configuration.

Clause 49: In some of the examples of the method of clause 48, the method further includes collapsing the stent to the collapsed configuration; repositioning the catheter within the fluid; re-expanding the stent to the partially expanded configuration; and delivering, using the energy source, an additional electrical signal between the primary electrode and the secondary electrode, where delivery of the additional electrical signal causes the fluid to undergo cavitation that results in the generation of a pressure pulse wave within the fluid.

Clause 50: In some of the examples of the method of clause 49, where collapsing the stent to the collapsed configuration includes advancing the outer elongated member distal relative to the inner elongated member such the outer elongated member forces the stent into the collapsed configuration.

Clause 51: In some of the examples of the method of any one of clauses 48 to 50, the method further includes retracting the outer elongated member relative to the inner elongated member such that the distal end of the outer elongated member is proximal to the proximal end of the stent; and deploying the stent in the expanded configuration within the fluid; and removing the catheter from the fluid.

Clause 52: In some of the examples of the method of clause 51, where deploying the stent in the expanded configuration within the fluid includes deploying the stent adjacent a heart valve or across the heart valve.

Clause 53: In some of the examples of the method of any one of clauses 48 to 51, further including introducing a distal portion of the catheter through vasculature of a patient to a target treatment site containing a calcified lesion.

Clause 54: In some of the examples of the method of any one of clauses 47 to 53, where delivering the electrical signal includes delivering, using the energy source, a plurality of electrical pulses having a pulse width of between about 1 microsecond (μs) and about 200 μs.

Clause 55: In some of the examples of the method of any one of clauses 47 to 54, the method further includes deploying an embolic protection device downstream of the stent prior to delivering the electrical signal.

The details of one or more examples are set forth in the accompanying drawings and the description below. Other features, objects, and advantages of examples according to this disclosure will be apparent from the description and drawings, and from the claims.

DETAILED DESCRIPTION

Figure 1A:
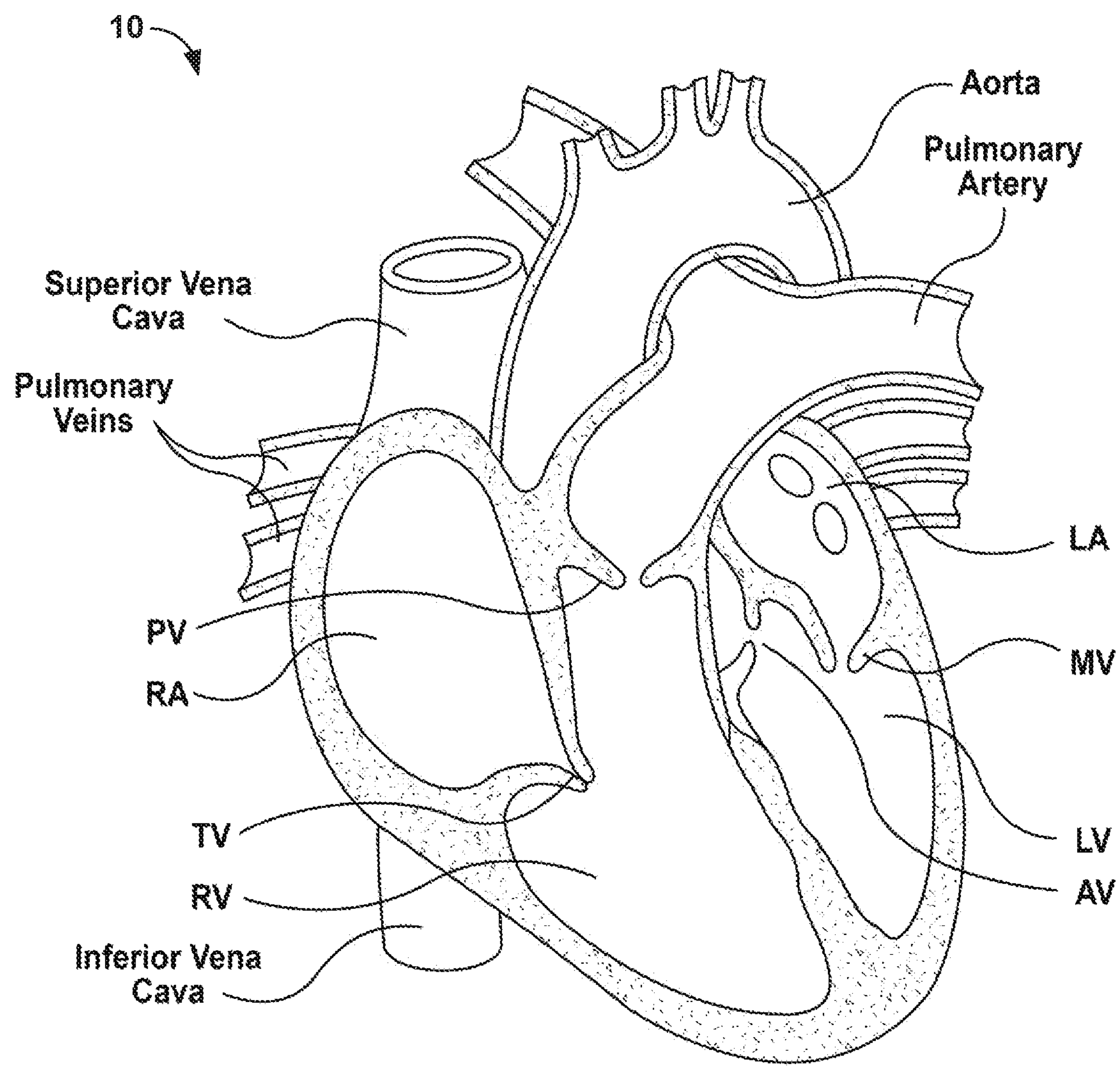
FIGS. 1A and 1B are schematic cross-sectional views of an example human heart.

This disclosure describes medical stents and medical assemblies for delivering and using the medical stents (also referred to herein as "stents"). The stents are configured to be implanted in cardiovasculature (e.g., in vasculature or a heart) of a patient and can be, for example, part of a heart valve prosthesis or a stent configured to be implanted in a blood vessel of a patient to help improve patency of the vessel. As a point of reference, in the context of at least heart valve prostheses, the term "frame" is interchangeable with the term "stent"; the frame of a heart valve prosthesis serves as the "stent" of the present disclosure. The stents may be configured to expand from a collapsed configuration to an expanded configuration. The stents may each include one or more electrodes carried by the stent and configured to deliver an electrical signal to a fluid contained within the heart or vasculature of the patient (e.g., blood) or delivered to the heart or vasculature of the patient by the stent (e.g., saline). The energy transmitted to the fluid may rapidly heat the fluid to produce a short-lived gaseous steam/plasma bubble within the fluid that quickly collapses (e.g., cavitates), releasing energy in the form of a pressure pulse wave. The pulse wave may be used to treat a defect in the heart or vasculature of the patient at a target treatment site.

In some examples, the target treatment site may be a site within the heart or vasculature that has a defect that may be affecting blood flow. For example, the target treatment site may be a portion of a heart valve, such as an aortic valve or mitral valve, that includes a calcified lesion, e.g., calcified plaque buildup on or within the valve. The calcium buildup may occur with age as the heart valves accumulate deposits of calcium which is a mineral found the blood. As blood repeatedly flows over the affected valve, deposits of calcium can build up on or within the leaflets or cusps of the valve, resulting in a stiffening (e.g., reduced pliability) of the leaflets. This stiffening narrows the valve, creating a stenosis that can result in adverse physiological effects to the patient.

Calcified lesions in the cardiovasculature may be very hard (e.g., relative to a native valve or blood vessel) and difficult to treat using traditional methods, such as balloon angioplasty, stenting, thrombectomy, atherectomy, valvuloplasty, or other interventional procedures. Even with the introduction of a heart valve prosthesis, the calcification of the heart valve may create a hinderance to alleviating the stenosis and returning the heart valve to normal flow parameters. For example, the calcification may reduce the elasticity of the native heart valve, which may interfere with the ability of a prosthetic heart valve that is implanted proximate to or within an annulus of the native heart valve to expand a desirable amount and define a desired flow diameter.

In some examples, a cavitation procedure cavitation procedure using the stents and medical assemblies described herein may be performed in the fluid adjacent to the calcified lesion to produce pressure pulse waves within the fluid. The pressure pulse waves resulting from the may impact a calcified lesion (or other defect) at a target treatment site to fracture or disrupt at least part of the lesion. Following the cavitation, the tissue at the target treatment site (e.g., heart valve or blood vessel) may be easily expanded with the described stents or other suitable device, allowing the treatment site to be expanded to a larger flow diameter. In examples in which the stent is used to treat calcification on the leaflets of a heart valve, post-cavitation, the calcified leaflets may become more elastic, allowing for easier manipulation when deploying the stent. In addition, the more elastic native leaflets may better enable the stent of the prosthetic heart valve to expand more fully in place proximate to or within an annulus of the native heart valve, which may help prevent valvular leakage in the future.

Delivering the cavitation treatment via a stent may provide one or more advantages. For example, in some examples in which the stent forms part of a heart valve prosthesis, the heart valve prosthesis can be deployed across a native heart valve of a patient immediately after delivery of the cavitation, e.g., without an additional medical procedure using a separate medical device. The deployment of the heart valve prosthesis immediately following the cavitation procedure may help improve treatment efficacy and potential patient outcomes. Additionally, or alternatively, using the catheters described herein to perform the cavitation procedure may reduce or eliminate the need for additional devices or electrical components to be inserted or implanted within the body of the patient to complete the described procedures.

Figure 1B:
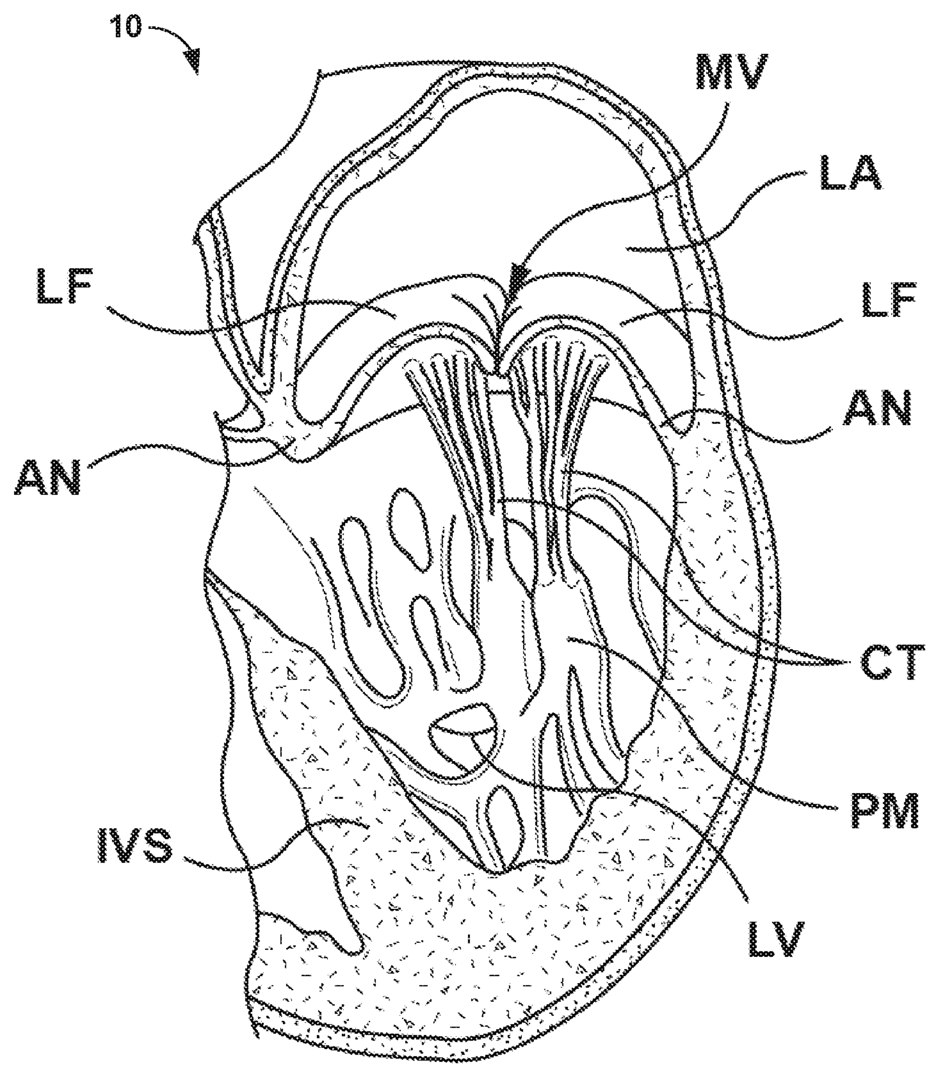

FIGS. 1A and 1B are schematic cross-sectional views of an example human heart 10. The human heart 10 is a four chambered, muscular organ that provides blood circulation through the body during a cardiac cycle. The four main chambers include the right atrium (RA) and right ventricle (RV) which supplies the pulmonary circulation, and the left atrium (LA) and left ventricle (LV) which supplies oxygenated blood received from the lungs to the remaining body. To ensure that blood flows in one direction through the heart, atrioventricular valves (tricuspid valve (TV) and mitral valves (MV)) are present between the junctions of the atrium and the ventricles, and semi-lunar valves (pulmonary valve (PV) and aortic valve (AV)) govern the exits of the ventricles leading to the lungs and the rest of the body. These valves contain leaflets (LF) or cusps that open and shut in response to blood pressure changes caused by the contraction and relaxation of the heart chambers. FIG. 1B is a schematic sectional illustration of a left ventricle LV of heart 10 showing anatomical structures and a native mitral valve MV.

The left atrium LA receives oxygenated blood from the lungs via the pulmonary veins and pumps the oxygenated blood through the mitral valve MV and into the left ventricle LV during ventricular diastole. The left ventricle LV contracts during systole and blood flows outwardly through the aortic valve AV, into the aorta and to the remainder of the body. In a healthy heart, the leaflets LF of the native mitral valve MV meet evenly at the free edges or "coapt" to close and prevent back flow of blood into the left atrium LA during contraction of the left ventricle LV. The tissue of the leaflets LF attach to the surrounding heart structure via a dense fibrous ring of connective tissue called an annulus AN. The flexible tissue of the leaflets LF of the native mitral valve MV are connected to papillary muscles PM, which extend upwardly from the lower wall of the left ventricle LV and the interventricular septum IVS, via branching tendons called chordae tendinae CT. In a heart 10 having a calcified plaque buildup, the leaflets LF of the valves (e.g., aortic valve AV or mitral valve MV) may harden and may not sufficiently coapt or meet, such that regurgitation may occur where the valve does not close completely, allowing blood to flow backwards (e.g., from the left ventricle LV to the left atrium LA). The left side of heart 10 (e.g., mitral valve MV and aortic valve AV) can be more likely to become calcified because of the higher pressures generated. The introduction of a heart valve prosthesis may address some of the inefficiencies of the leaflets LF but may have little or not effect on reducing the calcified buildup or alleviating the stenosis caused by the buildup.

The medical assemblies described herein may be used to treat such calcified plaque buildup on or within a heart valve by cavitating the fluid in the vessel or portion of the heart to generate pulse waves within the fluid to mechanically fracture or dislodge the calcifications. Once fractured or dislodged, the targeted treatment site may be more easily expanded to a normal flow diameter or function.

In some examples, the delivery catheters and methods are presented for the treatment of such heart valves as part of a procedure for minimally invasive implantation of a stent such as a stent that forms part of an artificial or prosthetic heart valve). For example, in accordance with the examples described below, the medical assemblies described herein can be used to percutaneously direct and deliver a mitral or aortic valve prosthesis via an intravascular retrograde approach.

Figure 2A:
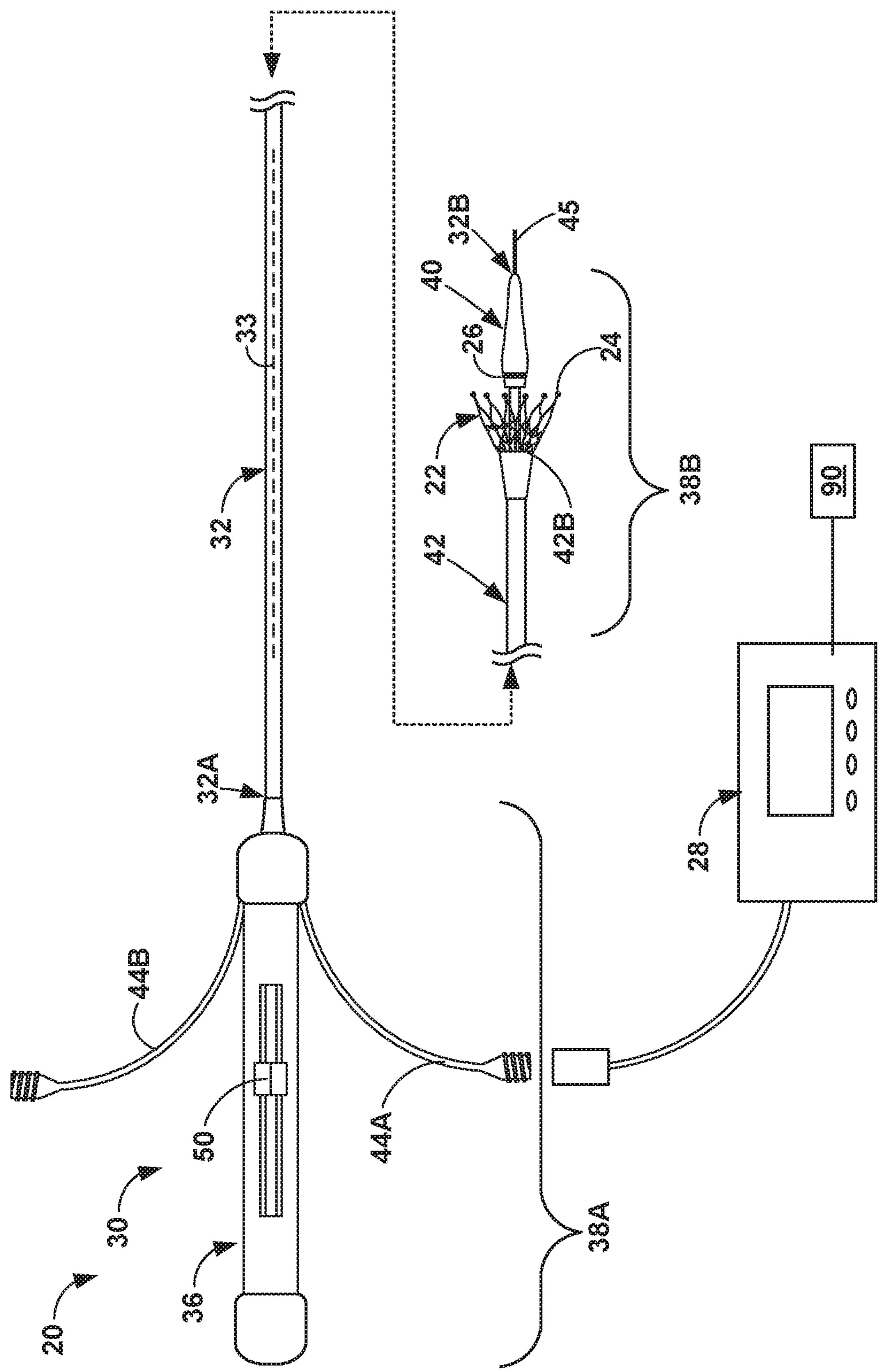
FIGS. 2A-2C are schematic side views of an example medical assembly, which includes a stent comprising at least one primary electrode, a secondary electrode, and an energy source configured to deliver an electrical signal between the primary and secondary electrodes to cause a fluid to undergo cavitation.
Figure 2B:
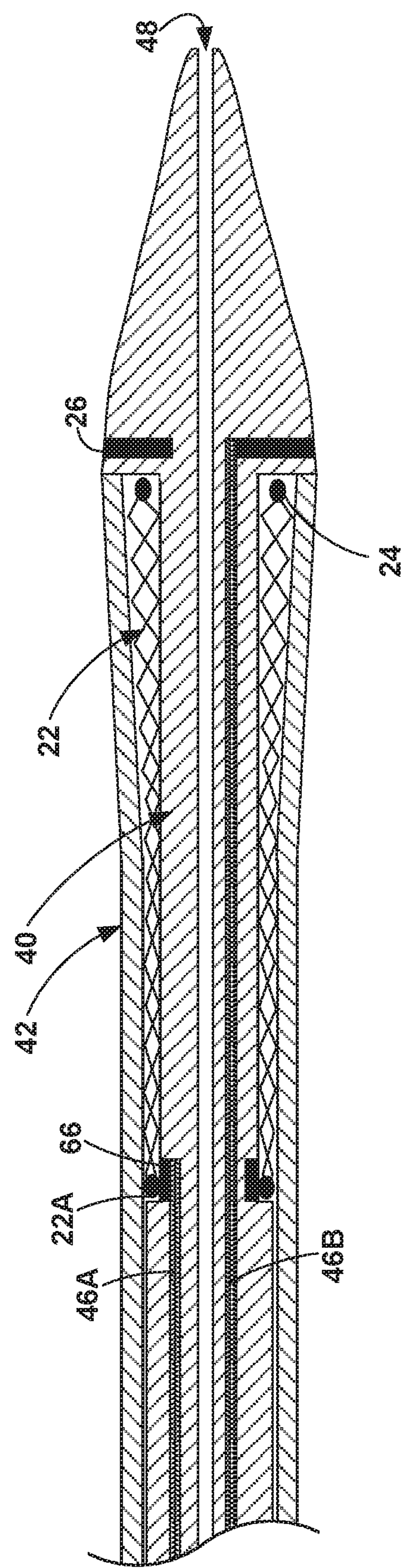
Figure 2C:
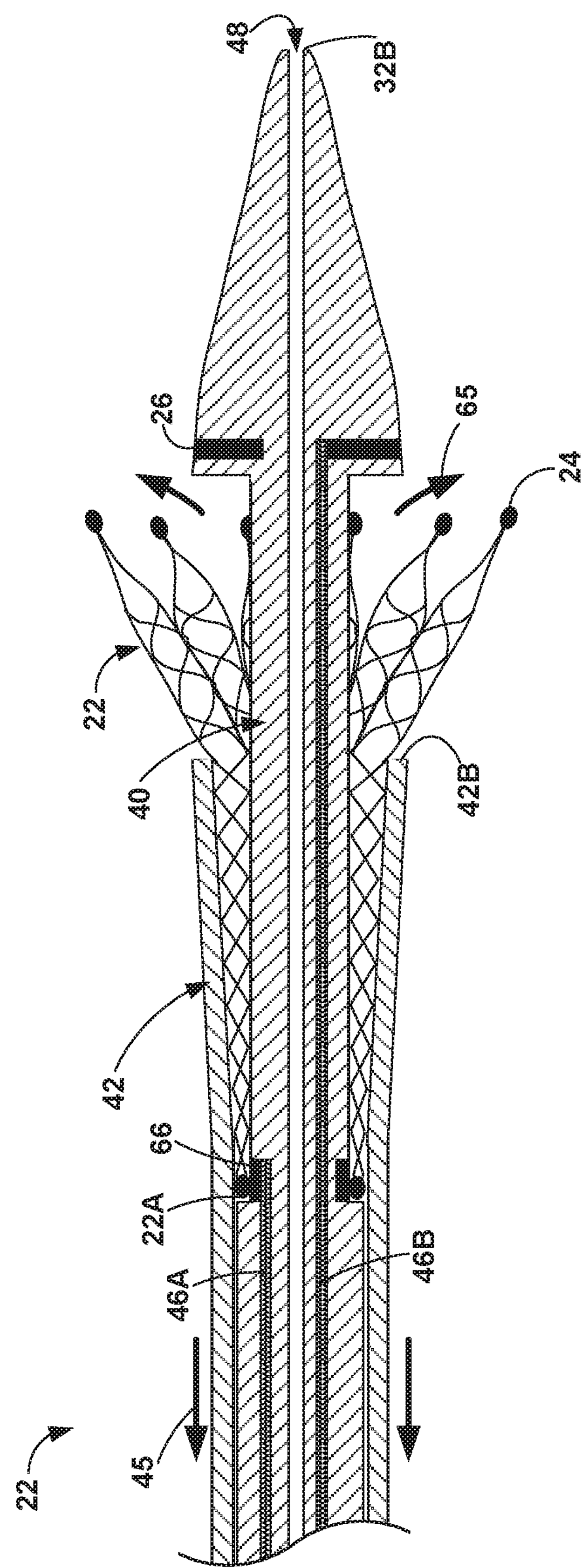

FIGS. 2A-2C are schematic side views of an example medical assembly 20, which includes a stent 22 comprising at least one primary electrode 24, a secondary electrode 26, and an energy source 28 configured to deliver an electrical signal between primary electrode 24 and secondary electrode 26 through a fluid in contact with primary electrode 24 to cause the fluid to undergo cavitation to generate a pressure pulse wave within the fluid. The designation of a "primary" or a "secondary" electrode is used to merely differentiate one set of electrodes from another and is not intended to indicate a preference among the electrodes, limit the direction in which an electrical signal is transmitted from one electrode to another, or designate where the cavitation initiates unless described otherwise in the examples. Further the term "electrode" may refer to the component(s) or portions of the component(s) that are used to induce cavitation within a fluid and is not intended to describe the entire cavitation system.

Stent 22 and primary electrode 24 may have any suitable configuration. In some examples, primary electrode 24 is an integral part of stent 22, while in other examples, primary electrode 24 is separate from and mechanically connected to stent 22. In some examples, stent 22 includes a metallic body and a dielectric coating applied over a portion of the metallic body. At least one surface of the metallic body may be exposed to the external environment of stent 22 (e.g., exposed to fluid within a blood vessel or a heart of a patient), and this exposed surface of the metallic body may define primary electrode 24. In some examples, stent 22 may include a plurality of primary electrodes 24, with each primary electrode 24 being defined by an exposed surface of the metallic body of stent 22. Additionally, or alternatively, the metallic body of stent 22 may be electrically coupled to a electrically conductive coating exposed to the external environment of stent 22 that defines at least one primary electrode 24.

Stent 22 is configured to expand from a collapsed configuration to an expanded configuration at a target treatment site within cardiovasculature of a patient. In some examples, stent 22 may be configured to self-expand from the collapsed configuration to the expanded configuration. For example, the metallic body of stent 22 may be composed of a shape memory or super-elastic material such as nickel-titanium (e.g., Nitinol) configured to self-expand to the expanded configuration when stent 22 is unconstrained. In other examples, stent 22 may be forcibly expanded from the collapsed configuration to the expanded configuration using a suitable device such as an expansion balloon. In some examples, stent 22 may form part of a heart valve prosthesis such as a mitral or an aortic valve prosthesis. As understood by one of ordinary skill, in the context of at least a heart valve prosthesis, the term "frame" is interchangeable with the term "stent"; the "frame" of a heart valve prosthesis serves as the "stent" of the present disclosure. In other examples, stent 22 may be a stand alone stent, e.g., used to improve patency of a blood vessel.

As shown in FIG. 2A, stent 22 may be mechanically connected to a catheter 30 configured to deliver stent 22 to target treatment site within the heart or vasculature of the patient. Catheter 30 may include an elongated member 32 extending from proximal end 32A to distal end 32B. The side view of catheter 30 shown in FIGS. 2A-2C illustrates catheter 30 along a longitudinal axis 33 of elongated member 32. FIGS. 2B and 2C are schematic cross-sectional side views of the distal portion of catheter 30 providing greater detail of some of the aspects of medical assembly 20, the cross-section being taken in a direction parallel to longitudinal axis 33. FIGS. 2B shows stent 22 positioned in a fully collapsed configuration within elongated member 32 of catheter 30 and FIG. 2C shows stent shows stent 22 positioned in a partially expanded configuration, e.g., upon proximal retraction of outer elongated member 42 relative to inner elongated member 40 (e.g., indicated by arrows 45), which are described in further detail below. As described further below, primary electrode 24 of stent 22 may be electrically couple to energy source 28 via catheter 30 while in the fully collapsed and partially expanded configurations.

Catheter 30 may include a hub portion 36 connected to proximal end 32A of elongated member 32. Hub portion 36, including proximal end 32A of elongated member 32, forms part of a proximal portion 38A of catheter 30. Catheter 30 also includes a distal portion 38B that includes distal end 32B of elongated member 32. The designations of proximal and distal portion 38A and 38B are used to describe different regions of catheter 30 (as divided along a length of catheter 30) and may be of any suitable length. In some examples, elongated member 32 may also be characterized as having one or more intermediate portions separating the proximal and distal portions 38A and 38B.

Elongated member 32 includes an inner elongated member 40 and outer elongated member 42 configured to be retracted relative to inner elongated member 40 (e.g., depicted by arrows 45). In some examples, inner elongated member 40 may be positioned within an axial lumen defined by outer elongated member 42. The two members 40, 42 may be configured to slide longitudinally, e.g., in the direction of longitudinal axis 33 relative to each other.

While the description primarily describes outer elongated member 42 as being configured to be retracted or advanced relative to inner elongated member 40, the description is not intended to imply or limit outer elongated member 42 as being the only moveable part within catheter 30. The retraction or advancement of outer elongated member 42 relative to inner elongated member 40 may be performed by the proximal and distal movement of outer elongated member 42, the proximal and distal movement of inner elongated member 40, or a combination of both. For example, in some examples, inner elongated member 40 may be moved distally (e.g., moved further from hub portion 36) to actuate the movement of outer elongated member 42 being retracted relative to inner elongated member 40. In other examples, outer elongated member 42 may be moved proximally (e.g., moved closer to hub portion 36) to actuate the movement of outer elongated member 42 being retracted relative to inner elongated member 40. Both types of configurations are envisioned by the characterization of outer elongated member 42 being configured to retract relative to inner elongated member 40. As described further below, the reaction and advancement of outer elongated member 42 relative to inner elongated member 40 may be actuated via a control member 50 positioned on hub portion 36.

Elongated member 32 may also include one or more electrical conductors 46A and 46B (collectively, "electrical conductors 46"). Electrical conductors 46A and 46B are configured to electrically couple primary or secondary electrodes 24 and 26, respectively, to energy source 28. In some examples, electrical conductors 46 may be electrical wires such as about 0.005 inch wires (about 0.13 mm) extending within inner or outer elongated members 40 and 42 (e.g., embedded within a wall of inner or outer elongated members 40 and 42 or within a lumen defined by inner or outer elongated members 40 and 42). Other diameters, either greater or lesser than 0.005 inch (0.13 mm) are also envisioned, for example in the range of 0.001-0.010 inch (0.0254-0.254 mm). Electrical conductors 46 may have any suitable configuration. In some examples, the wires forming electrical conductors 46 may be braided, coiled, or linearly extended along of inner or outer elongated members 40 and 42. Additionally, or alternatively, electrical conductors 46 may contribute or form part of the support structure (e.g., a coil and/or a braid) of inner or outer elongated members 40 and 42. Electrical conductors 46 may be electrically insulated from one another by an electrically insulating sheath or by the body of elongated members 40 and 42 which may be comprised of electrically non-conductive material (e.g., fluorinated ethylene propylene (FEP)). As shown in FIG. 2B, in some examples, both electrical conductors 46A and 46B may be carried by inner elongated member 40.

Assembly 20 also includes secondary electrode 26, which may be positioned relative to primary electrode 24 to generate cavitation within a fluid in communication (e.g., thermal communication) with primary electrode 24. In the example shown in FIGS. 2A-2C, distal portion 38B of elongated member 32 includes secondary electrode 26, which may be carried by either inner elongated member 40 or outer elongated member 42. As used herein "carried by" or "carried along" is used to describe electrode configurations in which the electrode is attached, connected, or adhered directly or indirectly to part of elongated member 32 or extends within or is embedded within elongated member 32. In other examples, secondary electrode 26 may not be carried by elongated member 32, but, rather, can be on a separate device (e.g., a guide member, such as a guidewire).

In some examples, secondary electrode 26 may define at least one surface that is exposed to the external environment of catheter 30 (e.g., exposed to an external fluid) when stent 22 is in the partially expanded configuration (FIG. 2C). Secondary electrode 26 may be constructed of any suitable material. In some examples, secondary electrode 26 may include an electrically conductive ring positioned over inner elongated member 40. Additionally, or alternatively, secondary electrode 26 may define an exterior surface of the distal tip of inner elongated member 40 adjacent distal end 32B of elongated member 32, or other type of surface that is exposed to fluid within the heart or vasculature of the patient during described cavitation process.

In some examples, secondary electrode 26 may be carried by a radially expandable member (e.g., a balloon or other device) connected to inner elongated member 40 or may be configured to self-expand (e.g., constructed with a shape memory material). The radial movement of secondary electrode 26 may help reduce the separation gap between primary electrodes 24 and secondary electrode 26 during the cavitation procedure, which may be useful for producing certain types of electrical discharges.

Inner elongated member 40 may also define a guidewire lumen 48 configured to receive guidewire 45 used to help navigate distal portion 38B to a target treatment site. For example, the guidewire may be introduced through vasculature of a patient to a target treatment site and distal portion 38B of catheter 30 may be advanced over the guidewire to navigate elongated member 32 through the vasculature of the patient to the target treatment site.

Proximal end 32A of elongated member 32 may be received within hub portion 36 and can be mechanically connected to hub portion 36 by any suitable technique. Hub portion 36 may include one or more supply tubes 44A and 44B (collectively "supply tubes 44"). Supply tubes 44 may provide access to the various components of distal portion 38B of elongated member 32 and may be used for accessing or transporting various items through elongated member 32 including, for example, a guidewire 45, a fluid for use during the cavitation procedure, one or more electrical conductors 46, a fluid for inflating or deflating a balloon (if present) carried by catheter 30, or the like. For example, one or more of the supply tubes (e.g., supply tube 44A) may be used to electrically couple primary and secondary electrodes 24 and 26 to energy source 28 via electrical conductors 46. Additionally, or alternatively, one or more of supply tubes 44 may be used to perfuse or aspirate portions of the vessel or heart at a target treatment site, used to introduce guidewire 45 into a guidewire lumen 48 of inner elongated member 40, or the like.

In some examples, catheter 30 may include a strain relief body, which may be a part of hub portion 36 or may be separate from hub portion 36. The strain relief body may extend distally from hub portion 36 and may help reduce mechanical strain between hub portion 36 and elongate member 32. Additionally, or alternatively, proximal portion 38A of catheter 30 can include another structure in addition or instead of hub portion 36. For example, catheter hub portion 36 may include one or more luers or other mechanisms for establishing mechanical connections, fluidic connections, or other types of connections between catheter 30 and other devices.

Hub portion 36 may include a control member 50 configured to actuate the movement (e.g., retraction and advancement) of outer elongated member 42 relative to inner elongated member 40 to permit the release of stent 22. Control member 50 may have any suitable design including, for example, a slider, a lever, or a thumbwheel mechanism that when actuated causes the proximal advancement or retraction of either inner elongated member 40 or outer elongated member 42 relative to the other. For example, control member 50 may be in the form a slider where moving the slider towards distal end 32B, causes outer elongated member 42 to slide proximal relative to the distal end 32B. Control member 50 may include one or more deployment markers that indicate when inner and outer elongated member 40 and 42 are aligned to permit partial expansion of stent 22 (e.g., where distal end 42B of outer elongated member 42 is proximal to a distal end 22B of stent 22 and distal to a proximal end 22A of stent 22), full expansion of stent 22 (e.g., where distal end 42B of outer elongated member 42 is proximal to proximal end 22A of stent 22), or full collapse of stent 22 (e.g., where distal end 42B of outer elongated member 42 is at or distal to distal end 22B of stent 22).

In some examples, elongated member 32 of catheter 30 may be used to access relatively distal treatment locations in a patient or other relatively distal tissue sites (e.g., relative to the access point for catheter 30). Example treatment locations may include, for example, locations at or near the heart or a heart valve (e.g., aortic valve, mitral valve, or the like) or within the blood vessels of a patient. In some examples, elongated member 32 is structurally configured to be relatively flexible, pushable, and relatively kink- and buckle-resistant, so that it may resist buckling when a pushing force is applied to a relatively proximal portion of catheter 30 to advance elongated member 32 distally through vasculature, and/or so that it may resist kinking when traversing around a tight turn in the vasculature. Unwanted kinking and/or buckling of elongated member 32 may hinder a clinician's efforts to push the catheter body distally, e.g., past a turn in the vasculature.

Elongated member 32 has a suitable length for accessing a target treatment site within the patient from the vasculature access point. The length may be measured along the longitudinal axis of elongated member 32. The working length of elongated member 32 may depend on the location of the lesion within the patient's body. For example, if catheter 30 is a catheter used to access a target treatment site at or adjacent a heart valve from a femoral access point, elongated member 32 may have a working length of about 50 centimeters (cm) to about 200 cm, such as about 110 cm, although other lengths may be used. In other examples, or for other applications, the working length of elongated member 32 may have different lengths.

The outer diameter of elongated member 32 may be of any suitable size or dimension including, for example, between about 1 millimeter (mm) and about 12 mm. In some examples, the outer diameter may be substantially constant (e.g., uniform outer diameter), tapered (e.g. tapered or step change to define a narrower distal portion), or combinations thereof.

In some examples, at least a portion of an outer surface of elongated member 32 (e.g., the outer surface of outer elongated member 42) may include one or more coatings, such as, but not limited to, an anti-thrombogenic coating, which may help reduce the formation of thrombi in vitro, an anti-microbial coating, and/or a lubricating coating. In some examples, the entire working length of elongated member 32 is coated with the hydrophilic coating. In other examples, only a portion of the working length of elongated member 32, e.g., including distal portion 38B, may be coated with the hydrophilic coating. This may provide a length of elongated member 32 distal to hub portion 36 that does not include a hydrophilic coating and with which the clinician may grip elongated member 32, e.g., to rotate elongated member 32 or push elongated member 32 through vasculature. In some examples, the entire working length of elongated member 32 or portions thereof may include a lubricious outer surface, e.g., a lubricious coating. The lubricating coating may be configured to reduce static friction and/or kinetic friction between elongated member 32 and tissue of the patient as elongated member 32 is advanced through the vasculature.

In some examples, elongated member 32 may also include one or more radiopaque markers which may help a clinician determine the positioning of elongated member 32 relative to a target treatment site. For example, one or more radiopaque markers may be positioned proximal, within, or distal to the housing area for stent 22, adjacent to secondary electrodes 26, or combinations thereof In some examples, portions of stent 22, primary electrodes 24, or secondary electrode 26 themselves may be radiopaque.

Figure 3:
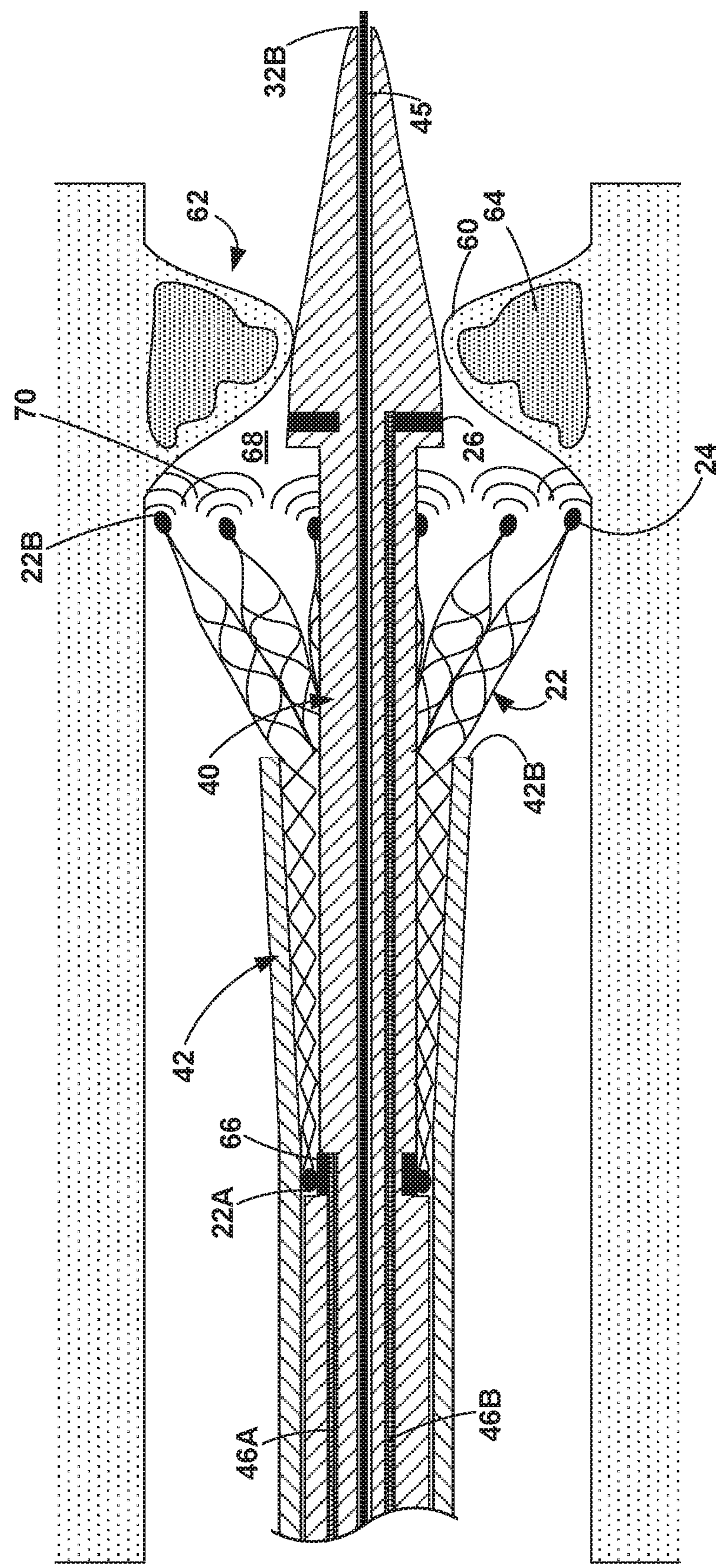
FIG. 3 is an enlarged conceptual cross-sectional view of the distal portion of the catheter of FIG. 2A positioned adjacent a target treatment site with the stent in a partially expanded configuration.

FIG. 3 is an enlarged conceptual cross-sectional view of distal portion 38B of catheter 30 of FIG. 2A, where the cross-section is taken along longitudinal axis 33 of elongated member 32. FIG. 3 shows distal portion 38B of catheter 30 positioned adjacent to a target treatment site 62 containing a calcified lesion 64 with stent 22 in a partially expanded configuration. In some examples, target treatment site 62 may be within vasculature of a patient, e.g., an artery or a vein. In other examples, target treatment site 62 may represent a native heart valve 60 (e.g., aortic valve or mitral valve) that includes calcified lesion 64, which may be calcium buildup on, adjacent, or within native heart valve 60, causing a heart valve stenosis (e.g., aortic stenosis). In some examples, calcified lesion 64 may affect the function of leaflets LF or cusps that open and shut heart valve 60 in response to blood pressure changes. For example, calcified lesion 64 may reduce the pliability of leaflets LF, thereby reducing blood flow through the native heart valve 60 and hindering heart valve 60 from functioning properly. The location of calcified lesion 64 in FIG. 3 is one example, and lesion 64 may be have another location such as a superficial or a deep calcification on or within the tissue of the heart or vasculature of the patient.

As shown in FIG. 3, distal portion 38B of elongated member 32 may be introduced through the vasculature of a patient and positioned adjacent to target treatment site 62. Outer elongated member 42 may be partially retracted relative to inner elongated member 40 such that distal end 42B of outer elongated member 42 is positioned proximal to distal end 22B of stent 22 and distal to proximal end 22A. Distal end 22B of stent 22 may then expand to a partially expanded configuration (e.g., indicated by arrows 65 in FIG.

2C). In some examples, distal end 22B of stent 22 may be configured to self-expand radially outwards, while in other examples, as described further below, distal end 22B may be expanded with the assistance of a balloon.

While in the compressed and partially expanded configurations, primary electrode 24 is electrically coupled to energy source 28 via catheter 30. For example, a portion of the metallic body of stent 22 (e.g., a portion near proximal end 22A) may be electrically coupled to electrical conductor 46A. Electrical conductor 46A may be in direct contact with the metallic body of stent 22 or may be electrically coupled to the metallic body of stent 22 through electrical contact with an intermediate electrically conductive component such as electrical contact 66. Electrical contact 66 may define a surface of either inner elongated member 40 or outer elongated member 42 configured to be in direct contact with the metallic body of stent 22 while stent 22 is in the partially expanded configuration. Electrical contact 66 may be connected to electrical conductor 46A via soldering or other suitable means to provide an electrical pathway between energy source 28 and primary electrode 24 using electrical conductor 46A and the metallic body of stent 22. In some examples, electrical contact 66 may include an electrically conductive ring positioned over inner elongated member 40 such that electrical contact 66 defines an external conductive surface of inner elongated member 40.

In some examples, inner elongated member 40 may also include a retaining member configured to receive at least a portion of stent 22. The retaining member is configured to help retain stent 22 in place relative to inner elongated member 40 while stent 22 is in the partially expanded configuration, such as by limiting or even eliminating rotational and longitudinal movement of stent 22 relative to inner elongated member 40. For example, the retaining member may define one or more shaped recesses configured to receive parts of proximal end 22A of stent 22 (e.g., connecting members or tabs) and prevent rotational or longitudinal movement of stent 22 while outer elongated member 42 is positioned over proximal end 22A of stent 22. In some examples, the retaining member may be formed in a wall of inner elongated member 40, in a wall of electrical contact 66, or by some other suitable device connected to inner elongated member 40. In addition, in some examples, electrical contact 66 may be positioned within the retaining member, such that when stent 22 is mechanically engaged with the retaining member, primary electrode 24 is electrically connected to conductor 46A via the electrical contact 66. Example retaining members are described in commonly owned U.S. Pat. No. 6,814,746, entitled, "IMPLANT DELIVERY SYSTEM WITH MARKER INTERLOCK," U.S. Patent No. 9,044,351, entitled, "IMPLANT AND DELIVERY SYSTEM WITH MULTIPLE MARKER INTERLOCKS," U.S. Pat. No. 6,623,518, entitled, "IMPLANT DELIVERY SYSTEM WITH INTERLOCK," and U.S. patent application Ser. No. 15/919,973, entitled, "MEDICAL DEVICE DELIVERY SYSTEM INCLUDING A SUPPORT MEMBER," the entire content of each of which is incorporated by reference herein.

Once the cavitation procedure has been completed, outer elongated member 42 may be retracted relative to inner elongated member 40 such that distal end 42B of outer elongated member 42 is proximal of proximal end 22A of stent 22. At that time, the retaining member may release stent 22 allowing the stent to be deployed in the expanded configuration at the target treatment site. As a consequence of being deployed, stent 22 will become disconnected from electrical contact 66 and electrical conductor 46A, thereby allowing stent 22 to remain in the body of the patient and catheter 30, along with all the other electrical components of catheter 30 to be removed from the body of the patient. In some examples, the separation may occur naturally once proximal end 22A of stent 22 is allowed to expand within valve 60, while in other examples proximal end 22A may be partially mechanically coupled (e.g., via a friction clip) to electrical contact 66 and the connection may be severed with a small amount of force (e.g., the force produced by stent 22 returning to the expanded state or by the retraction of elongated member 32).

From the partially expanded configuration, energy source 28 may deliver, using catheter 30, an electrical signal between primary electrode 24 and secondary electrode 26. The electrical signal may be delivered through a fluid 68 via primary and secondary electrodes 24 and 26 to heat a portion of fluid 68 to generate a steam/plasma bubbles within fluid 68. The steam/plasma bubbles may represent relatively low-pressure pockets of vapor generated from the surrounding fluid 68. The low-pressure steam/plasma bubbles eventually collapse in on themselves due to the relatively high pressure of the surrounding fluid 68 and heat loss of the steam/plasma bubbles to the surrounding fluid 68. As the steam/plasma bubbles collapse, the bubbles release a large amount of energy in the form of a high-energy pressure pulse waves 70 within fluid 68. In some examples, the formation and subsequent collapse of the steam/plasma bubbles may be short lived or nearly instantaneous, causing the pressure pulse waves 70 to originate near the source of energy delivered to fluid 68 by primary or secondary electrode 24 or 26.

The electrical signal transmitted may be delivered as a corona, an electrical arc, a spark, or the like between primary and secondary electrodes 24 and 26 using fluid 68 as the conductive media. In some examples, secondary electrode 26 may represent the return electrode such that the current density along the exposed surface area (e.g., exposed to fluid 68) of secondary electrode 26 is maximized. Additionally, or alternatively, the exposed surface areas of primary electrode 24 (e.g., the portion of the metallic body of stent 22 defining primary electrode 24) may be relatively small to maximize the current density on the exposed surface. In some examples, the size or material of respective primary and secondary electrodes 24 and 26 selected to accommodate the desired current. In some examples, the respective exposed surface of each primary electrode 24 may be less than about 0.1 square millimeters ($mm^2$) to provide the surface for the formation of the plasma/steam bubbles to occur.

In some examples, the separation distance between primary electrode 24 and secondary electrode 26 may be set depending on the type of electrical signal intended to be transmitted between the electrodes. For example, for arc-type cavitation, primary electrode 24 and secondary electrode 26 may be separated by a distance of about 0.005 inches to about 0.020 inches (e.g., about 0.13 mm to about 0.5 mm). For corona-type cavitation, primary electrode 24 and secondary electrode 26 may be separated by a distance of about 0.005 inches to about 0.050 inches (e.g., about 0.13 mm to about 1.3 mm), or may be separated by even larger distances.

Once formed within fluid 68, the pressure pulse waves 70 may propagate through fluid 68 where they impact the afflicted tissue transmitting the mechanical energy of the pressure pulse wave into the tissue and calcified lesion 64. The energy transmitted to calcified lesion 64 may cause the calcium buildup to fracture or break apart allowing target treatment site 62 to be subsequently expanded (e.g., via stent 22 and/or a balloon) to a larger flow diameter.

By conducting the cavitation procedure within fluid 68 in direct and intimate contact with the calcified lesion 64, the transfer of energy from the pressure pulse waves 70 to calcified lesion 64 may be more efficient as compared to a cavitation procedure that introduces one or more intermediate devices, such as a sidewall of a balloon that may otherwise dampen the pulse energy, between the source of cavitation (e.g., primary and secondary electrodes 24 and 26) and calcified lesion 64. In some examples, the improved efficiency of the process may require less energy to be transmitted to fluid 68 to incur the same amount of cavitation forces. Further, as the temperature of fluid 68 will increase as a consequence of the cavitation procedure, reducing the overall energy delivered to fluid 68 may also help reduce the temperature increase to fluid 68 caused by the delivery of energy to fluid 68.

The more efficient transfer of energy from the pressure pulse waves 70 to calcified lesion 64 may also reduce the duration that the cavitation procedure must be performed in order to sufficiently fracture or break apart calcified lesion 64 resulting in an overall shorter procedure. In some examples, by cavitating fluid 68 directly in contact with target treatment site 62, the space provided at the treatment site may allow for the resultant plasma bubbles to grow before collapsing which may help increase the resultant pressure created by the pressure pulse waves 70.

Additionally, by conducting cavitation using partially expanded stent 22 rather than a fully expanded stent 22 (in which case stent 22 would be mechanically disconnected from elongated member 32), stent 22 may be easily repositioned within fluid 68 relative to target treatment site 62 to provide additional cavitation treatment. For example, after a round of initial cavitation while stent 22 is in the partially expanded configuration, outer elongated member 42 may be advanced distally relative to inner elongated member 40 to force stent 22 into the collapsed configuration against inner elongated member 40. While in the collapsed configuration, distal portion 38B of catheter 30 may be repositioned relative to fluid 68 and target treatment site 62. Stent 22 may then be re-deployed into the partially expanded configuration by retracting outer elongated member 42 relative to inner elongated member 40 and the cavitation procedure may be repeated. The entire process may be repeated as many times as necessary. In some example, the ability to reposition stent 22 and primary electrode 24 relative to target treatment site 62 may permit the treatment of multiple calcified lesions within the cardiovasculature of the patient or may permit treating a relatively large lesion from multiple positions and/or directions.

Conducting cavitation using stent 22 also permits stent 22 rather than a separate cavitation device may also enable stent 22 to be implanted at target treatment site 62 following the cavitation procedure without needing to use a separate device (e.g., stent delivery catheter) to complete the delivery of stent 22, making the overall procedure more efficient.

In some cases, the calcification of calcified lesion 64 may not release into a blood stream of a patient. In other cases, however, at least some calcification may break away from lesion 64 and create emboli that releases into a blood stream of a patient. In some examples, the cavitation procedure may be performed in conjunction with an embolic protection element, e.g., a filter device, positioned downstream of target treatment site 62 to collect emboli and any potions of calcified lesion 64 that may be dislodged by pressure pulse waves 70. The embolic protection element can be any suitable device, including, but not limited to, a blood permeable membrane or wire mesh mechanically connected to an elongated member.

As described further below, in some examples, stent 22 may include a plurality of primary electrodes 24, which may be distributed about stent 22. The plurality of primary electrodes 24 may be electrically connected together (e.g., in series or parallel) or may be electrically isolated from each other and electrically connected to respective electrical conductors 46. The plurality of primary electrodes 24 may have any suitable configuration, and can be an integral part of stent 22 or may be separate from stent 22 and mechanically connected to stent 22. For example, each respective primary electrode 24 may be defined by a surface of the metallic body of stent 22 being exposed to fluid 68. In some examples, plurality of primary electrodes 24 may be positioned at distal end 22B of stent 22 such that when stent 22 is in the partially expanded configuration, plurality of primary electrodes 24 are distributed in a ring pattern.

In some examples, by controlling the size of the exposed surfaces defining primary electrodes 24 relative to the larger exposed surface of secondary electrode 26, cavitation may occur near primary electrodes 24. The distributed ring pattern of plurality of primary electrodes 24 may provide more uniform and distributed energy at target treatment site 62 and better disruption of calcified lesion 64 by pressure pulse waves 70. Such ringed-pattern arrangements may be useful for targeting calcified lesion 64 adjacent or within native heart valve 60 of a patient. Additionally, or alternatively, primary electrode 24 may be defined by the apex of a distal strut of stent 22 or by one or more metal tabs extending from the distal strut to provide a relatively large exposed surface area for the electrode compared to the size of the respective struts. The larger exposed surface area of such electrodes 24 along with the curved apexes may help preserve the integrity of primary electrodes 24 during cavitation procedure by being less apt to separate or melt during the cavitation procedure due to the relatively high current loads.

Fluid 68 may include any fluid capable of undergoing cavitation via energy delivered to fluid 68 by primary electrode 24. In some examples, fluid 68 may be or include blood flowing within the patient. In addition to or instead of blood, in some examples, fluid 68 may be or include a fluid introduced into the patient, such as, but not limited to, biocompatible fluids such as saline, phosphate buffered saline (PBS), or similar solution with a salt content between about 0.9 weight percent (wt. %) and about 5 wt. %; contrast media (e.g., about 25 volume percent (vol. %) to about 75 vol. % contrast media), or the like. Saline or other ionic solutions may more readily undergo cavitation compared to blood, thereby requiring less energy to induce cavitation within fluid 68. For example, the higher the salt content of the saline fluid, the higher the conductance will be for the fluid, thereby requiring less energy to increase the temperature of the fluid and induce cavitation. Additionally, the higher the concentration of contrast media, the more viscous fluid 68 will be leading to a higher dissipation of the cavitation bubbles.

In some examples, fluid 68 may be heated (e.g., body temperature or about 37° C.) prior to introduction into the patient. Heating fluid 68 may increase the relative vapor pressure of the fluid and thus require less energy to induce cavitation. In these examples, fluid 68 may include fluid not found in the patient's body, but, rather, introduced by a clinician. In examples in which fluid 68 is introduced into the patient's body, fluid 68 may be introduced to target treatment site 62 using any suitable technique. In some examples, elongated member 32 may define one or more perfusion lumens configured to provide access to target treatment site 62 and permit the delivery of fluid 68, such as saline, into the vessel or heart via one of supply tubes 44 (FIG. 2A). For example, inner elongated member 40 may define a perfusion lumen with a port exiting near stent 22. Fluid 68 may be forced through the perfusion lumen (not shown) via one of supply tubes 44 where fluid 68 mixes with blood at target treatment site 62 and undergoes cavitation by electrodes 24 and 26.

In some examples, stent 22 may be configured to self-expand. For example, stent 22 may include a metallic body made of a shape memory or super-elastic material such as nickel titanium (e.g., Nitinol). In shape memory material may treated to cause stent 22 to expand to the partially and fully expanded configurations when released from a constrained condition within outer elongated member 42 to assume the predetermined partially and fully expanded configuration. In some examples, stent 22 may be configured to expand to a diameter of about 23 mm to about 34 mm.

Figure 4:
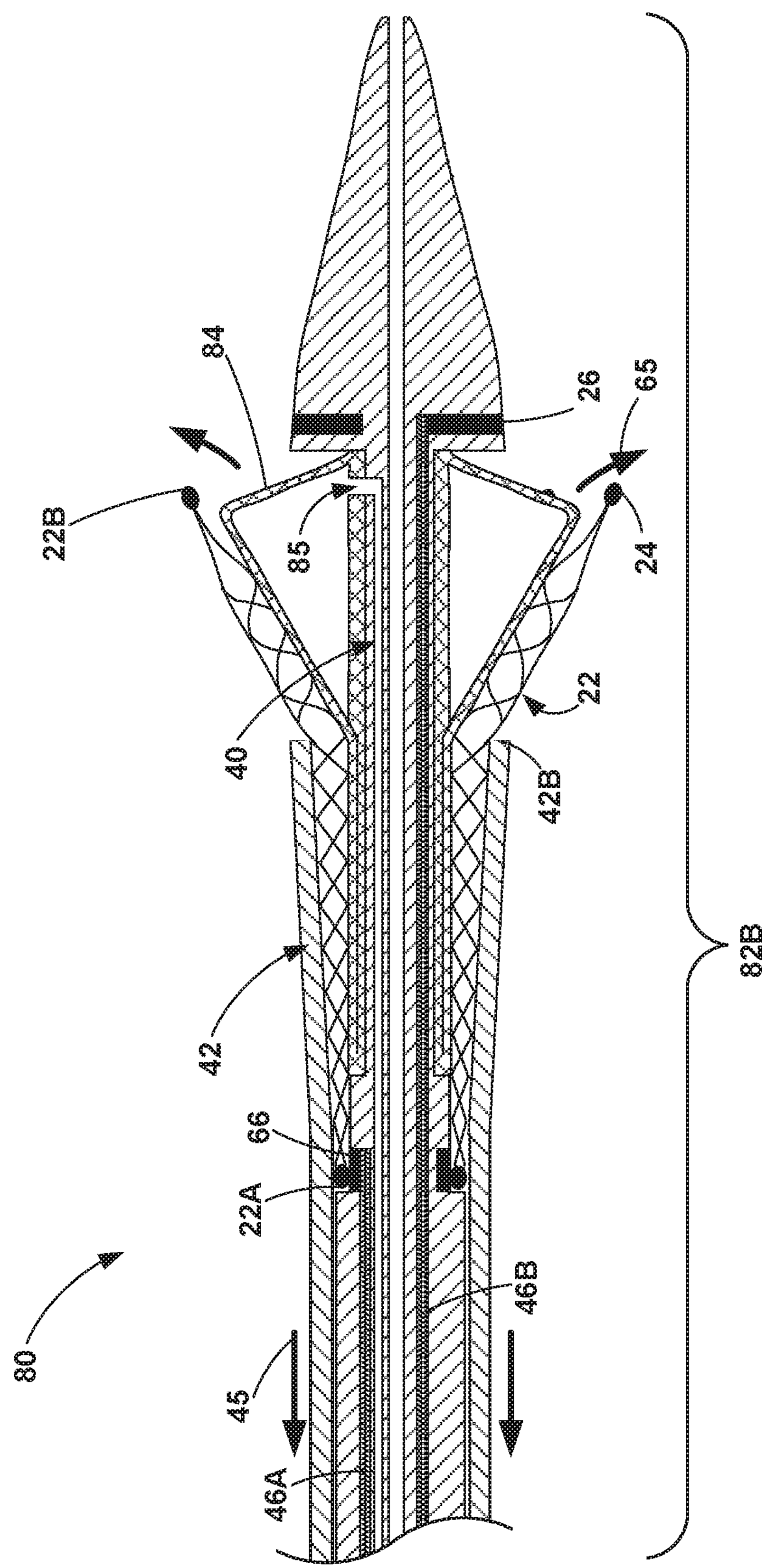
FIG. 4 is an enlarged conceptual cross-sectional view of an example distal portion of an elongated member that may be used with the catheter of FIG. 2A.

In other examples, stent 22 may be configured to be expanded with the aid of an expansion balloon or other mechanical expansion device mounted to inner elongated member 40. FIG. 4 is an enlarged conceptual cross-sectional view of an example distal portion 82B of an elongated member 80 that may be used with catheter 30 of FIG. 2A. Elongated member 80 includes inner and outer elongated members 40 and 42 with stent 22 positioned therebetween. FIG. 4 illustrates stent 22 in a partially expanded configuration, in which a proximal end of stent 22 is still positioned between inner and outer elongated members 40, 42. Elongated member 80 includes a balloon 84 attached to inner elongated member 40 and between inner elongated member 40 and stent 22. In some examples, outer elongated member 42 may represent a delivery sheath or may be excluded from elongated member 80. For example, outer elongated member 42 may be excluded and stent 22 may be crimped over balloon 84 during delivery of stent 22 to target treatment site 62.

Balloon 84 is configured to expand stent 22 to the partially expanded and/or fully expanded configurations at target treatment site 62. For example, with outer elongated member 42 retracted relative inner elongated member 40 such that distal end 42B of outer elongated member 42 is positioned proximal to distal end 22B of stent 22 and distal to proximal end 22A, balloon 84 may be partially inflated with a fluid via one of supply tubes 44 and inflation lumen 85 to forcibly expand distal end 22B of stent 22 to the partially expanded configuration. A cavitation procedure may then be performed with stent 22 in the partially expanded configuration. Following the cavitation procedure, stent 22 may be fully expanded and positioned at target treatment site 62 (e.g., at native heart valve 60) by retracting outer elongated member 42 relative inner elongated member 40 such that distal end 42B of outer elongated member 42 is positioned proximal to proximal end 22A of stent 22 and inflating balloon 84 to forcibly expand and deploy stent 22 at target treatment site 62. In some examples, stent 22 may be implanted adjacent or across leaflets LF of heart valve 60 (e.g., adjacent of across the annulus of the heart valve)

Balloon 84 may be formed from any suitable material, such as a flexible polymeric material that is configured to form a tight seal with inner elongated member 40. In some examples, balloon 84 may be formed physically separate from inner elongated member 40 and attached to an exterior surface of inner elongated member 40 via co-extrusion, bonding, adhesives, or the like. In other examples, balloon 84 may be integrally formed with inner elongated member 40 such that balloon 84 is embedded or at least partially embedded in inner elongated member 40. In other examples, balloon 84 may be separated from inner elongated member 40 such that balloon 84 forms a tight seal with itself.

Balloon 84 may be constructed using a flexible polymeric material including, for example, nylon 12, polyethylene, polyethylene terephthalate (PET), silicone, polyvinyl chloride, polypropylene, polyurethanes, polyamides, polyesters, latex, natural rubber, synthetic rubber, polyether block amides, or the like. Additionally, or alternatively balloon 84 may be constructed with an electrically insulative material.

In some examples, balloon 84 may be configured to be deflatable via a vacuum or other stable source to forcibly remove fluid from the balloon, thereby allowing for quicker collapse and/or a lower cross-sectional profile after the cavitation procedure is completed. Additionally, or alternatively, balloon 84 may include one or more perfusion ports allowing fluid to continuously flow from the balloon into the vessel or heart of the patient.

Balloon 84 may have any suitable size or shape. In some examples, balloon 84 may define a cross sectional diameter of about 30 mm to about 80 mm in the expanded configuration so that stent 22 may be deployed in the fully expanded configuration within heart valve 60 after the cavitation procedure. Balloon 84 may also have any suitable length (e.g., measured along longitudinal axis 33). For some procedures used to treat calcifications in or near heart valve 60 (e.g., aortic valve) of a patient, balloon 84 may define a length of about 15 mm to about 100 mm.

In some examples, balloon 84 may define one or more electrically conductive surfaces that electrically couple to stent 22. Electrical conductor 46A may be electrically connected to the electrically conductive surface of balloon 84 to connect stent 22, in particular primary electrodes 24, to power source 28. In this manner, the electrically conducive surface of balloon 84 may function in conjunction with, or in place of, electrical contact 66. Additionally, or alternatively, secondary electrode 26 may be carried by balloon 84 near a middle or distal part of balloon 84. In some such examples, the expansion of balloon 84 may likewise reposition secondary electrode 26 radially outward with stent 22 such that the separation gap between secondary electrode 26 and primary electrodes 24 of stent 22 remain relatively small (e.g., less than 0.5 mm) or relatively constant (e.g., constant separation gap or nearly constant separation gap), which may be useful for producing certain types of electrical discharges.

Figure 5:
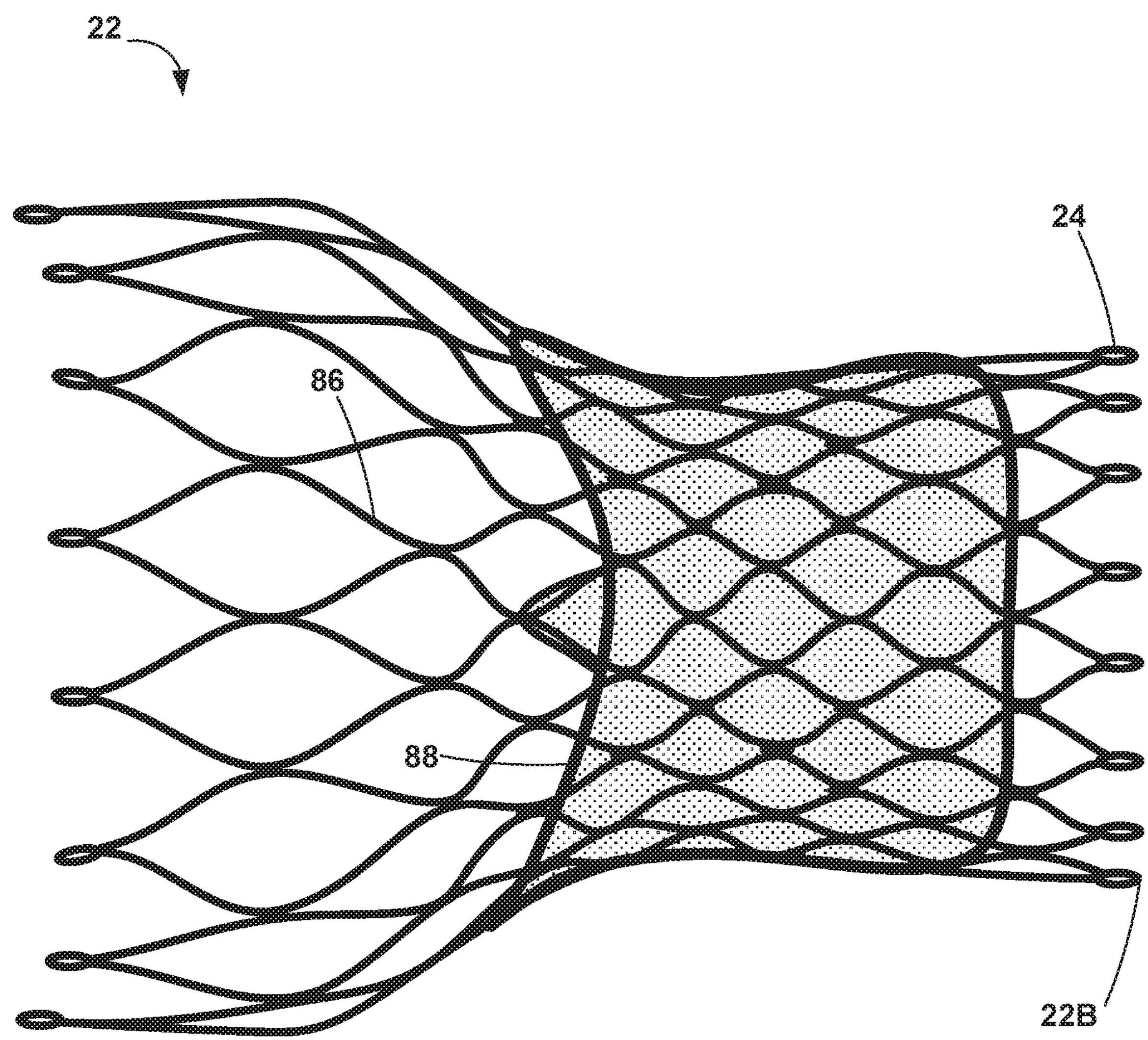
FIG. 5 is an example side view of the stent of FIG. 2A in a fully expanded configuration.

FIG. 5 is an example side view of stent 22 in a fully expanded configuration. In some examples, stent 22 may include a metallic body comprising a plurality of struts 86 that define any suitable pattern and cell structure (e.g., open cells or closed cells). For example, struts 86 may define a serpentine, zig-zag, or accordion-like pattern. In other examples, struts 86 of stent 22 may have other configurations, such as one or more compressible coils. Additionally, or alternatively, stent 22 may include a plurality of metallic filaments braided into a tubular body.

As mentioned above, the metallic body of stent 22 may include any suitable metal or metal alloy including, but not limited to nickel titanium alloy, stainless steel, cobalt chromium alloy, or the like. In examples in which stent 22 is self-expanding, the metallic body of stent 22 may include a shape memory material, such as nitinol, capable of delivering an electrical signal to fluid 68 to induce cavitation. Portions of the metallic body of stent 22 may be electrically insulated from fluid 68 (FIG. 3) by a dielectric or electrically non-conductive coating, such as, but not limited to, parylene or FEP, over the metallic body. The dielectric coating may be removed (e.g., laser removal or mechanically cut or etched) or excluded from portions of stent 22 defining the at least one primary electrode 24 and portions that electrically couple to electrical contact 66 or other electrical conductors. In some examples, the dielectric coating may be removed or excluded from the distal end 22B of stent 22 to define one or more primary electrodes 24. In other examples, the one or more primary electrodes 24 may be defined by other portions of the metallic body of stent 22. Additionally, the dielectric coating may be removed or excluded from one or more portions of stent 22 (e.g., near proximal end 22A or near portions of stent 22 contacting the annulus of valve 60) define the electrical contact point between the metallic body of stent 22 and electrical contact 66 of elongated member 32 or other electrical conductors coupled to stent 22. In some examples, the metallic body of stent 22 provides the electrical pathway between the primary electrode and the electrical contact 66 or electrical conductor coupled to stent 22.

In some examples, stent 22 may form part of a heart valve prosthesis. In such examples, stent 22 may include one or more additional components such as an artificial heart valve member 88 (e.g., including valve leaflets), a mounting ring, or the like attached to the body of stent 22. As shown in FIG. 5, in examples in which stent 22 is part of a heart valve prostheses, stent 22 may define a waist that configures stent 22 to be positioned within an annulus of native heart valve 60. In some examples, the waist may configure stent 22 to self-seat within the annulus of native heart valve 60.

In other examples, stent 22 may be used to improve patency in a blood vessel of a patient. In these examples, stent 22 may not define a waist, but, rather, may be configured to be more tubular in shape (e.g., a tube defining a constant diameter in the absence of any compressive or expansive forces).

Figure 6:
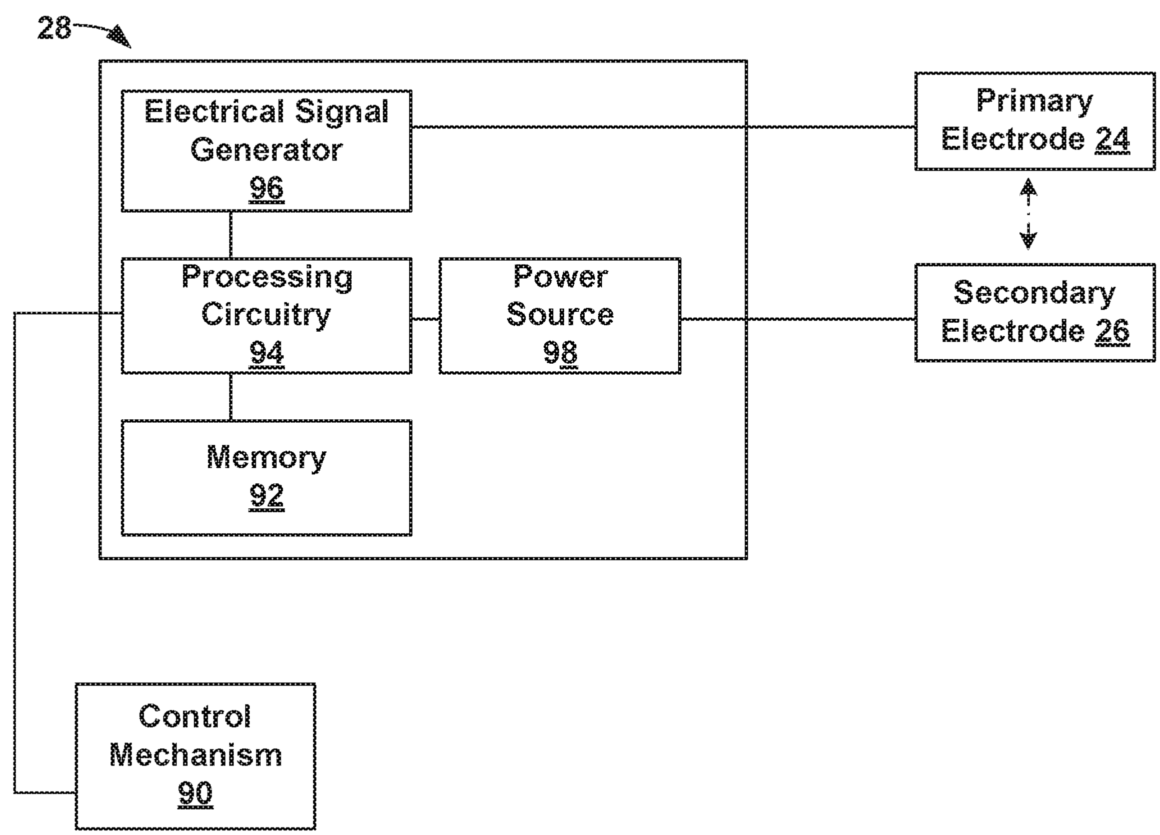
FIG. 6 is a schematic block diagram of an example energy source that may be used with the medical assemblies and stents described herein to induce cavitation within a fluid.

FIG. 6 is a schematic block diagram of an example energy source 28 that may be used with the medical assemblies and stents described herein to induce cavitation within fluid 68 (FIG. 3). Energy source 28 includes control mechanism 90, memory 92, processing circuitry 94, electrical signal generator 96, and power source 98.

Processing circuitry 94 may include any one or more microprocessors, controllers, digital signal processors (DSPs), application specific integrated circuits (ASICs), field-programmable gate arrays (FPGAs), discrete logic circuitry, or any processing circuitry configured to perform the features attributed to processing circuitry 94. The functions attributed to processors described herein, including processing circuitry 94, may be provided by a hardware device and embodied as software, firmware, hardware, or any combination thereof. In some examples, processing circuity 76 may include instructions to recognize a particular electrode configuration or allow a clinician to manually input the specific electrode configuration. In some examples, energy source 28 may include additional components such as, a display device or user input device that are not expressly shown for displaying information from processing circuitry 94 or allowing the clinician to input information.

Memory 92 may include any volatile or non-volatile media, such as a random access memory (RAM), read only memory (ROM), non-volatile RAM (NVRAM), electrically erasable programmable ROM (EEPROM), flash memory, and the like. Memory 92 may store computer-readable instructions that, when executed by processing circuitry 94, cause processing circuitry 94 to perform various functions described herein. Memory 92 may be considered, in some examples, a non-transitory computer-readable storage medium including instructions that cause one or more processors, such as, e.g., processing circuitry 94, to implement one or more of the example techniques described in this disclosure. The term "non-transitory" may indicate that the storage medium is not embodied in a carrier wave or a propagated signal. However, the term "non-transitory" should not be interpreted to mean that memory 92 is non-movable. As one example, memory 92 may be removed from energy source 28, and moved to another device. In certain examples, a non-transitory storage medium may store data that can, over time, change (e.g., in RAM).

Processing circuitry 94 is configured to control energy source 28 and electrical signal generator 96 to generate and deliver the electrical signal between primary and secondary electrodes 24 and 26 to induce cavitation of fluid 68. Electrical signal generator 96 includes electrical signal generation circuitry and is configured to generate and deliver an electrical signal in the form of pulses and/or a continuous wave electrical signal. In the case of electrical pulses, electrical signal generator 96 may be configured to generate and deliver pulses having an amplitude of about 500 volts (V) to about 5000 V (e.g., between about 1500V to about 3000 V), a pulse width of about 1 microsecond (μs) to about 5 μs for arc-type cavitation or about 10 μs to about 200 μs for corona-type cavitation, and a frequency of about 0.5 Hertz (Hz) to about 5 Hz. In some examples, catheter 30 may be configured such that electrical conductors 46A and 46B are independently coupled to energy source 28. In some examples, the intensity of the pressure pulse waves 70 may be adjusted by controlling the intensity of the electrical signal delivered to primary and secondary electrodes 24 and 26. The intensity of the electrical signal may be function of one or more of a voltage, a current, a frequency (e.g., a pulse rate in the case of pulses), a pulse width, or one or more other electrical signal parameters.

Power source 98 delivers operating power to various components of energy source 28. In some examples, power source 98 may represent hard-wired electrical supply of alternating or direct electrical current. In other examples, power source 98 may include a small rechargeable or non-rechargeable battery and a power generation circuit to produce the operating power. Recharging may be accomplished through proximal inductive interaction between an external charger and an inductive charging coil within energy source 28.

A control mechanism 90, such as foot pedal, handheld, or remote-control device, may be connected to energy source 28 to allow the clinician to initiate, terminate and, optionally, adjust various operational characteristics of energy source 28, including, but not limited to, power delivery. Control mechanism 90 can be positioned in a sterile field and operably coupled to the energy source 28 and can be configured to allow the clinician to selectively activate and deactivate the energy delivered between primary and secondary electrodes 24 and 26. In other embodiments, control mechanism 90 may be built into hub portion 36.

Figure 7:
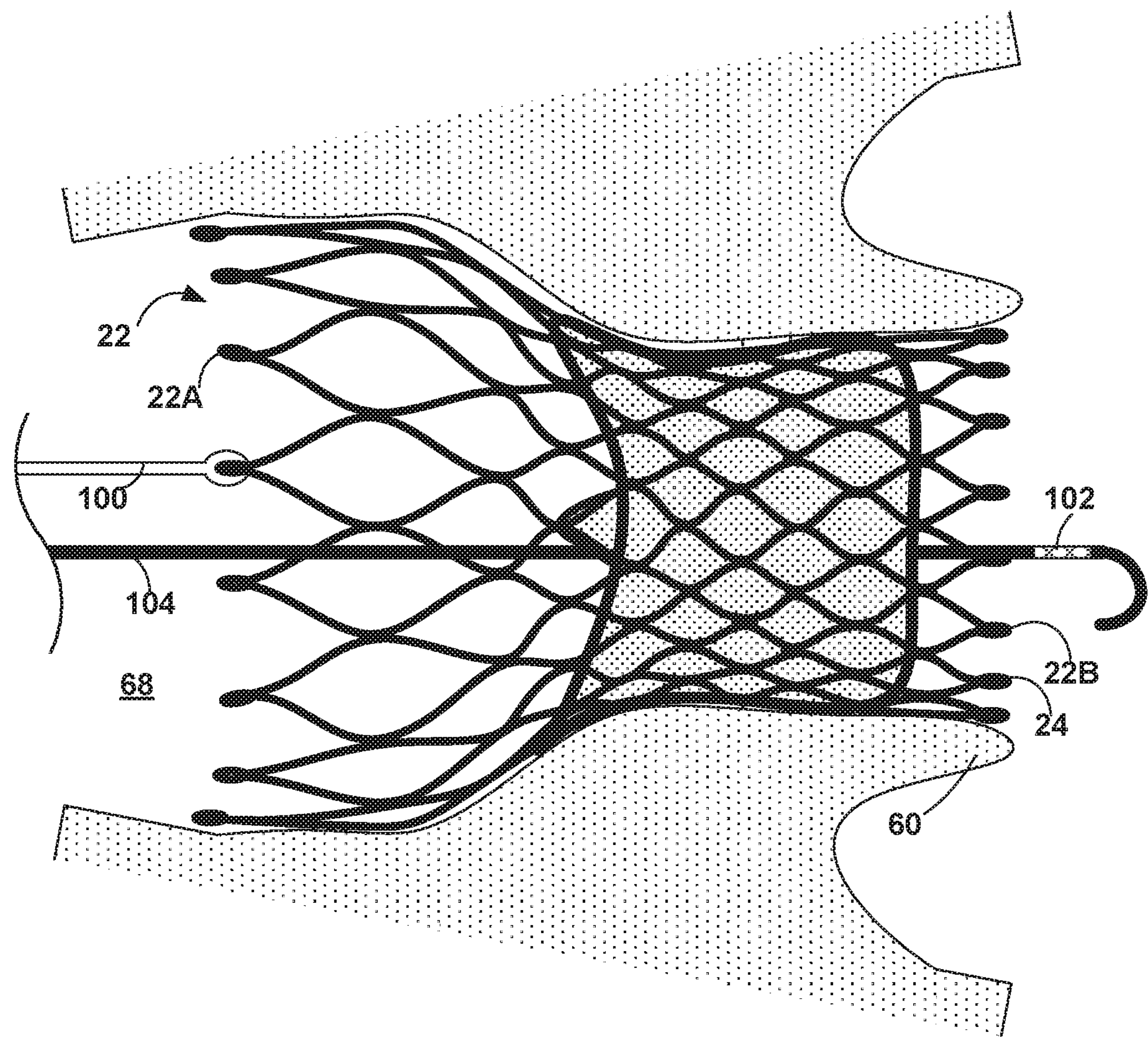
FIG. 7 is a schematic side view of another example medical assembly including a heart valve prosthesis implanted in a heart of a patient.

In some examples, stent 22 may be configured to induce cavitation of fluid 68 after stent 22 has been deployed at target treatment site 62 in its fully expanded configuration, in which it is mechanically disconnected from catheter 30. Generating cavitation at target treatment site 62 while stent 22 is in its expanded configuration may increase the force directed into calcified lesion 64 due to the structure of stent 22 acting as a force concentrator that impacts the adjacent tissue. FIG. 7 is a schematic side view of another example medical assembly including stent 22 deployed across native heart valve 60 of a patient. In some examples, heart valve 60 may be experiencing valvular insufficiency or regurgitation attributed to the valvular stenosis and/or calcium buildup. Even though the cavitation procedures described herein may help alleviate the calcium buildup or valvular stenosis, insufficiency of heart valve 60 may still necessitate the need for replacement of valve 60, e.g., with a transcatheter valve replacement procedure. As described above, stent 22 may include heart valve member 88 configured to provide a prosthetic replacement for heart valve 60. For example, heart valve member 88 may include non-native tissue that defines leaflets, a non-tissue mechanical valve, or any other suitable structure.

Primary electrode 24 of stent 22 may be electrically coupled to energy source 28 via electrical conductor 100. Electrical conductor 100 may be electrically coupled to the metallic body of stent 22 at, for example, proximal end 22A at an exposed surface of the metallic body or, in other examples, another portion of the metallic body.

Electrical conductor 100 may be any suitable conductor configured to electrically connect primary electrode 24 of stent 22 to energy source 28. In some examples, electrical conductor 100 may be an electrical wire comprising a dielectric coating or electrically insulative sheath over the wire apart from the proximal and distal ends of the wire that are electrically coupled to energy source 28 and stent 22 respectively.

Secondary electrode 102 may be provided by any suitable device coupled to energy source 28 and configured such that the delivery of the electrical signal between primary electrode 24 and the secondary electrode 102 causes fluid 68 in contact with primary electrode 24 to undergo cavitation. In the example shown in FIG. 7, secondary electrode 102 is carried by a guidewire 104. In other examples, secondary electrode 102 is carried by a different guide member, such as a catheter that defines an inner lumen through which a cavitation fluid 68 other than blood may be introduced at target treatment site 62.

Guidewire 104 may be positioned at target treatment site 62 such that secondary electrode 102 is positioned in contact with fluid 68 and adjacent to primary electrode 24. The proximal end of guidewire 104 may be electrically coupled to energy source 28 and the electrical signal may be transmitted between primary and secondary electrodes 24 and 102 to cause fluid 68 to undergo cavitation. Guidewire 104 may include any suitable style guidewire including, but not limited, a guidewire with a dielectric coating over guidewire 104 except for the portion of guidewire defining secondary electrode 102. Guidewire 104 may be substantially linear or may define a pigtail curve at its distal end. Guidewire 104 may eliminate the need for one of the electrical conductors 100 being attached to stent 22 while also providing a 360 degree formation of pressure pulse waves 70 at target treatment site 62.

In the example shown in FIG. 7, primary electrode 24 is depicted as being at distal end 22B of stent 22. In other examples, the one or more primary electrodes 24 may be defined by other portions of the metallic body of stent 22. For example, one or more primary electrodes 24 may be defined by an intermediate portion of stent 22 between proximal and distal ends 22A and 22B. In some examples, the metallic body of stent 22 may define a plurality of primary electrodes 24 in a circumferential ring about stent 22.

In other examples, the secondary electrode may be external to the patient. For example, the secondary electrode may be positioned on the external skin surface of the patient, e.g., as a pad or patch electrode and electrically coupled to energy source 28. The electrical signal may be delivered between primary electrode 24 and the secondary the electrode, through fluid 68 and the tissue of the patient to induce cavitation of fluid 68 at primary electrodes 24.

Figure 8:
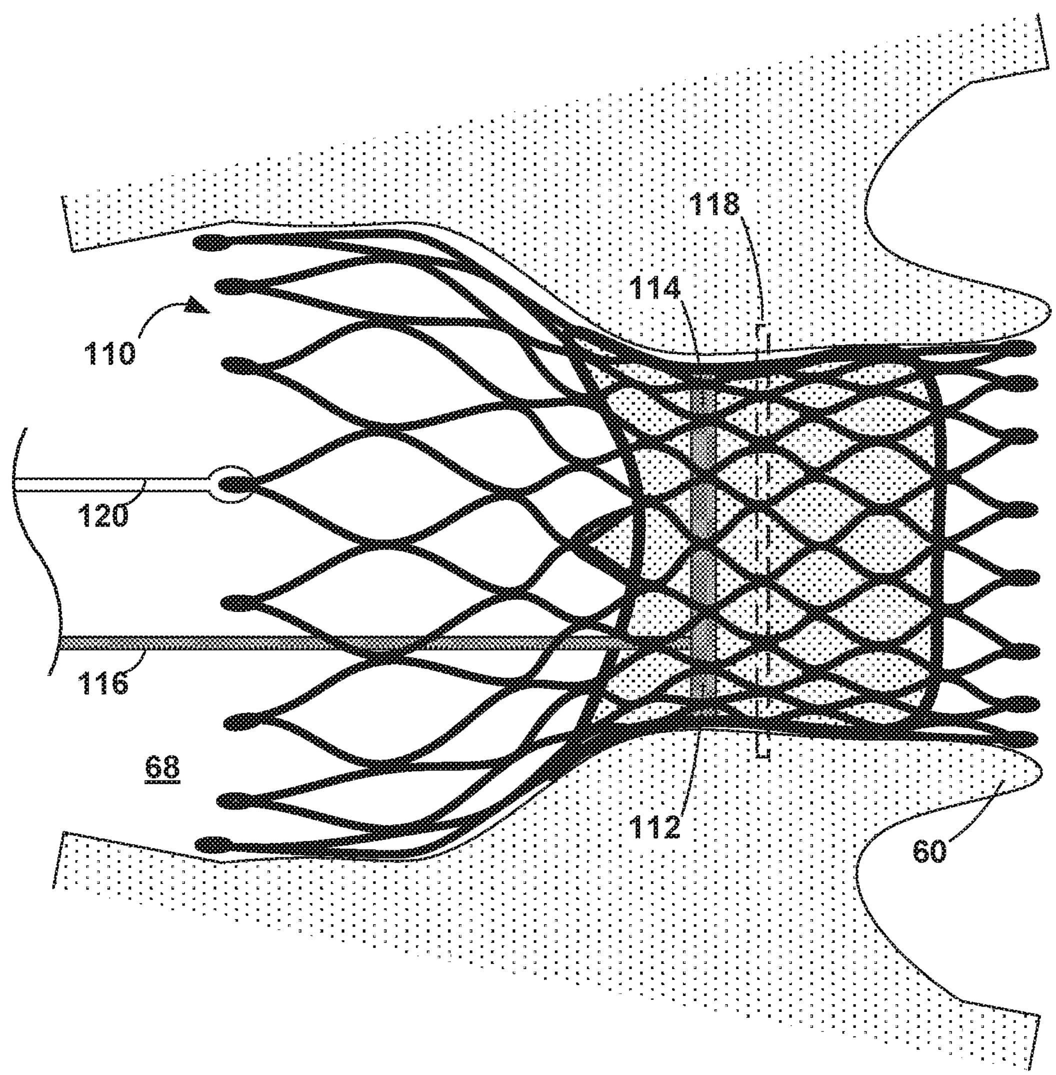
FIG. 8 is a schematic side view of another example medical assembly including a heart valve prosthesis implanted in a heart of a patient.

In other examples, the secondary electrode may be carried by stent 22. For example, FIG. 8 is a schematic side view of another example medical assembly including stent 110 deployed across heart valve 60. Stent 110 may be substantially the same (e.g., the same or nearly the same) as stent 22 but may further include an electrically conductive band 112 attached to a portion of stent 110. Electrically conductive band 112 may include a metallic ring or annulus attached to stent 110 such that the dielectric coating on stent 110 prevents direct contact between electrically conductive band 112 and the metallic body of stent 110. A surface of electrically conductive band 112 may define the secondary electrode 114. Electrically conductive band 112 may be electrically coupled to energy source 28 by an electrical conductor 116 connected to the metallic ring. In some examples, electrically conductive band 112 may also provide structural support to stent 110.

Stent 110 also includes one or more primary electrodes 118 defined by one or more exposed surfaces of the metallic body of stent 110. In the example shown in FIG. 8, primary electrodes 118 are defined by or attached to an intermediate portion of stent 110 that positioned between the proximal and distal ends of sent 110 where the metallic body is exposed to fluid 68. In other examples, primary electrodes 118 may be defined by or attached to other portions of the metallic body of stent 110. Primary electrodes 118 may be electrically coupled to energy source 28 by an electrical conductor 120 connected to the metallic body of stent 110.

Figure 9A:
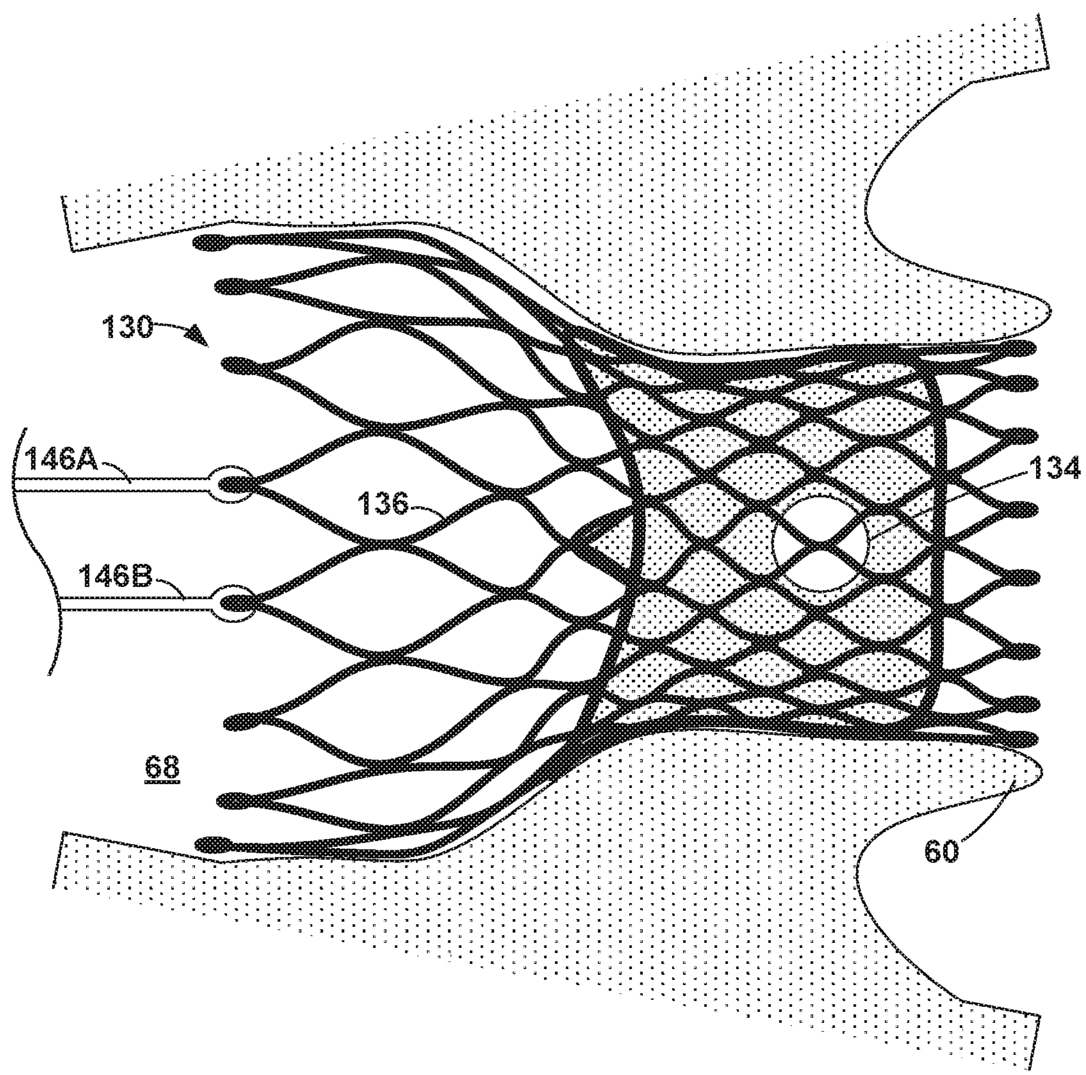
FIG. 9A is a schematic side view of another example medical assembly including a heart valve prosthesis implanted in a heart of a patient.
Figure 9B:
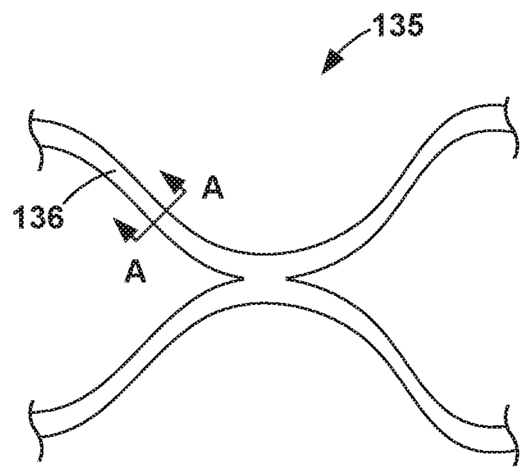
FIGS. 9B and 9C are different views of the stent of the heart valve prostheses of FIG. 9A.
Figure 9C:
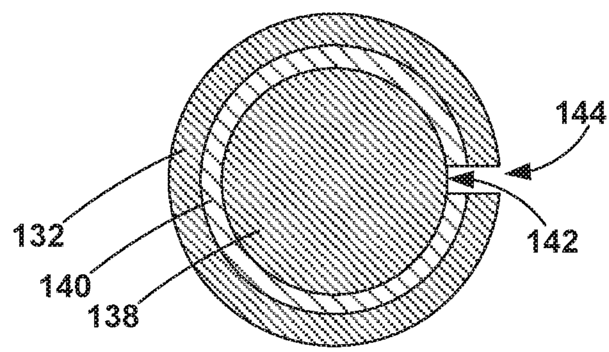

FIGS. 9A-9C are schematic views of another example medical assembly including stent 130 deployed across native heart valve 60 of a patient where the secondary electrode is defined by an electrically conductive coating 132 applied to stent 130.

FIG. 9A is a side view of stent 130 taken along its central axis, FIG. 9B is an enlargement of section 134 of FIG. 9A showing a close-up of struts 136 of stent 130, FIG. 9C is a cross-sectional view of strut 136 taken through line A-A of FIG. 9B.

Stent 130 may include a metallic body 138 including a plurality of struts 136. Metallic body 138 may include a dielectric coating 140 (e.g., parylene or FEP) over a portion of metallic body 138. Metallic body 138 may define at least one surface 142 that is exposed to the external environment of stent 130 (e.g., exposed to fluid 68) that defines at least one primary electrode. Dielectric coating 140 may cover portions of metallic body 138 and prevent direct contact between electrically conductive coating 132 and metallic body 138. In some examples, dielectric coating 140 and electrically conductive coating 132 may define an electrode aperture 144 that extends through a thickness of both coatings to expose surface 142 of metallic body 138 to expose surface 142 to fluid 68, thereby defining a respective primary electrode.

Electrically conductive coating 132 and metallic body 138 may each be electrically coupled to energy source 28 by electrical conductors 146A and 146B connected to the respective components. During a cavitation procedure, an electrical signal may be delivered between metallic body 138 and electrically conductive coating 132 using fluid 68 captured within electrode aperture 144 to induce cavitation of fluid 68. The electrical signal transmitted may form a corona, an electrical arc, a spark, or the like between the conductive surfaces using fluid 68 as the conductive media.

Electrode aperture 144 may take on any suitable shape and size. In some examples, the size and shape of electrode aperture 144 may guide the direction or size of the acoustic output of the pressure pulse waves 70. In some examples, electrode apertures 144 may be oriented in different circumferential directions along stent 130. Cavitation generated at the exposed surfaces of electrode apertures 144 may then produce pressure pulse waves 70 directed in different circumferential directions.

While stents 22, 110, and 120 in FIGS. 7-9C are illustrated and described as being deployed in the fully expanded configuration within heart valve 60, stents 22, 110, and 120 may be delivered by catheter 30 or used to induce cavitation of fluid 68 while stent 22, 110, and 120 is in a partially expanded configuration within stent 30. For example, the described electrical conductors 100, 116, 120, and 146 may be electrically coupled to the stent 22, 110, and 120 and/or carried by catheter 30, while the stent is in a partially expanded configuration. The cavitation procedure may then be performed between the described primary and secondary electrode configurations of any of the respective stents 22, 110, and 120 described herein. The respective stent may then be deployed within the cardiovasculature of the patient.

Figure 10:
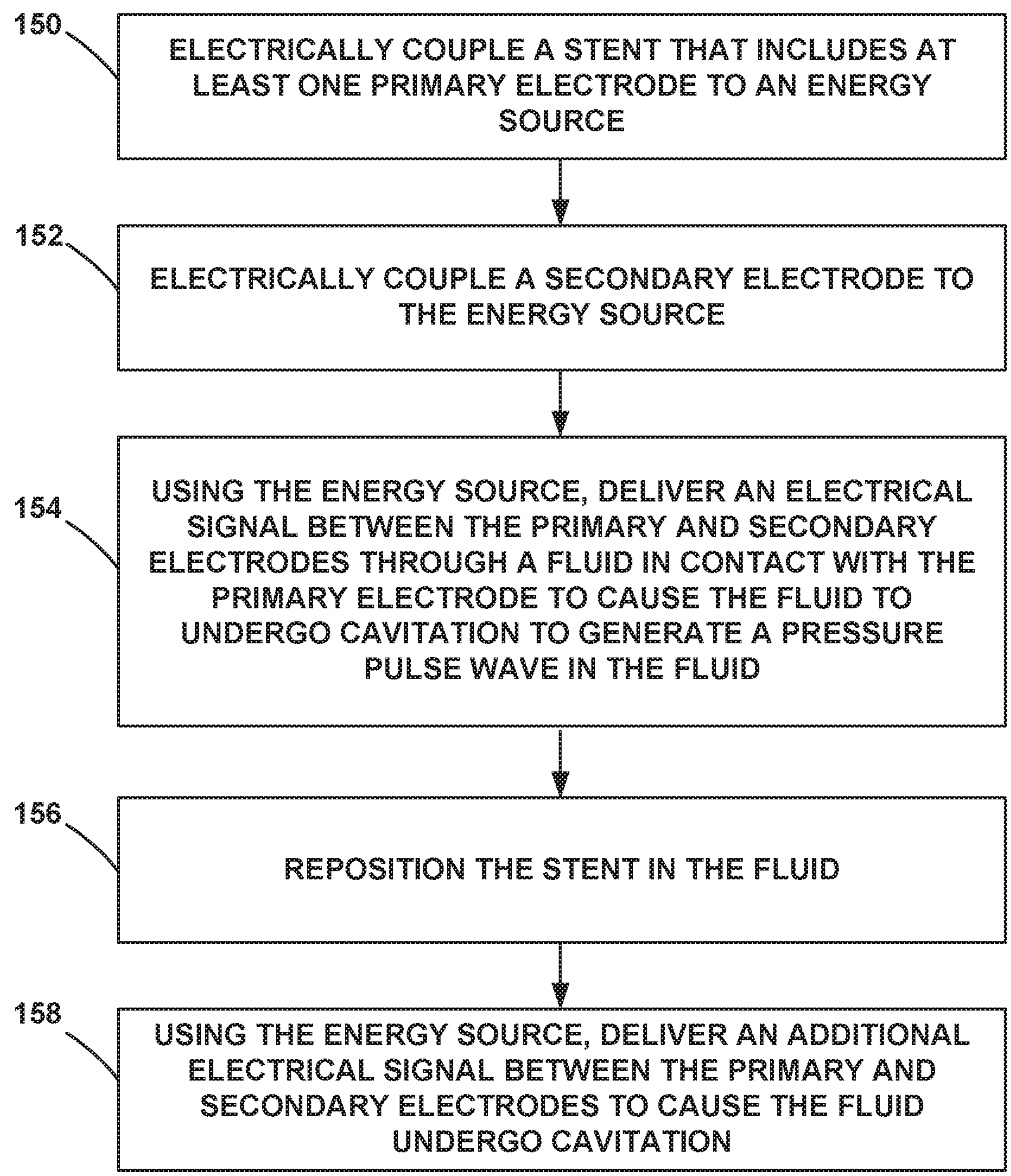
FIG. 10 is a flow diagram of an example technique of using the medical assemblies described herein.

FIG. 10 is a flow diagram of an example technique of using the medical assemblies described herein. For illustrative purposes, the techniques of FIG. 10 are described with reference to the various aspects of the medical assemblies of FIGS. 2A, 4, and 7-9C, however, such descriptions are not intended to be limiting and the techniques of FIG. 10 may be used with other medical assemblies or the medical assemblies of FIGS. 2A, 4, and 7-9C may be used in other applications.

The technique of FIG. 10 includes electrically coupling a stent 22, 110, 130 including at least one primary electrode 24, 116 to an energy source 28 (150); electrically coupling a secondary electrode 26, 102, 114 to energy source 28 (152); using energy source 28, delivering an electrical signal between primary electrode 24, 116 and secondary electrode 26, 102, 114 through a fluid 68 in contact with primary electrode 24, 116 to cause fluid 68 to undergo cavitation to generate a pressure pulse wave 70 in fluid 68 (154); optionally repositioning stent 22 within fluid 68 (156); and using energy source 28, deliver an additional electrical signal between primary electrode 24 and secondary electrode 26 through fluid 68 to cause fluid 68 to undergo cavitation (158).

As described above, in some examples, stent 22 and primary electrode 24 may be coupled to energy source 28 (150) via catheter 30. Stent 22 may be initially mounted within catheter 30 and delivered to target treatment site 62 (e.g., adjacent to or within an annulus of native heart valve 60) of a patient by catheter 30. Stent 22 may be initially positioned between inner and outer elongated members 40 and 42 of catheter 30. At target treatment site 62, stent 22 may be expanded to a partially expanded configuration such that primary electrode 24 is electrically coupled to energy source 28 via electrical conductor 46A and electrical contact 66 of catheter 30 while in the partially expanded configuration.

In some examples, stent 22, 110, 130 may be electrically coupled to energy source 28 by an electrical conductor 100, 120, 146A other than electrical conductor 46A carried by catheter 30. In some such examples, stent 22, 110, 130 may be in a partially expanded configuration within catheter 30 or a fully expanded configuration at target treatment site 62 and electrical conductor 100, 120, 146A may electrically couple stent 22, 110, 130 to energy source 28 while in the fully expanded configuration at target treatment site 62.

The technique of FIG. 10 also includes electrically coupling secondary electrode 26, 102, 114 to energy source 28 (152). As described above, in some examples, secondary electrode 26 may be carried by catheter 30 used to deliver stent 22 to target treatment site 62. In some such examples, secondary electrode 26 may include an electrically conductive ring or partial ring positioned over inner elongated member 40 of catheter 30 such that secondary electrode 26 may define an exterior surface of the distal tip of inner elongated member 40 adjacent distal end 32B of catheter 30. In such examples, secondary electrode 26 may be electrically coupled to energy source 28 via electrical conductor 46B carried by elongated member 32 of catheter 30.

In other examples, the secondary electrode may be carried by the stent 110, 130 itself. For example, stent 110 may include electrically conductive band 112 attached to a portion of stent 110 that defines the secondary electrode 114. Electrically conductive band 112 may be electrically coupled to energy source 28 by an electrical conductor 116 connected to electrically conductive band 112. In other examples, a secondary electrode may be defined by electrically conductive coating 132 applied to stent 130. In both instances, the dielectric coating of stent 110, 130 may prevent direct contact between the underlying metallic body and the secondary electrode being carried by stent 110, 130.

In yet other examples, the secondary electrode may be carried by a separate device, such as guidewire 104 carrying secondary electrode 102 or an external pad mount to the patient's skin and electrically coupled separately to energy source 28.

Once primary electrode 24, 116 and secondary electrode 26, 102, 114 have been electrically coupled to energy source 28, energy source 28 may deliver an electrical signal between primary electrode 24, 116 and secondary electrode 26, 102, 114 through fluid 68 in contact with at least primary electrode 24, 116 to cause fluid 68 to undergo cavitation to generate pressure pulse waves 70 in fluid 68 (154). As described above, primary electrode 24, 116 and secondary electrode 26, 102, 114 may transmit energy to fluid 68 (e.g., electrical energy) that rapidly heats a portion of fluid 68 to produce short-lived gaseous steam/plasma bubbles within fluid 68. The steam/plasma bubbles may represent relatively low-pressure pockets of vapor generated from the surrounding fluid 68. The low-pressure steam/plasma bubbles eventually collapse in on themselves due to the relatively high pressure of the surrounding fluid 68. As steam/plasma bubbles collapse, the bubbles release a large amount of energy in the form of a high-energy pressure pulse wave within fluid 68 that propagate through fluid 68 where they impact calcified lesion 64 transmitting the mechanical energy of pressure pulse waves 70 into the tissue and calcified lesion 64. The energy transmitted to calcified lesion 64 may cause the lesion to fracture or beak apart.

In some examples, the electrical energy delivered to fluid 68 via primary electrode 24, 116 and secondary electrode 26, 102, 114 may be in the form of a corona, an electrical arc, a spark or the like. The electrical signal may be a continuous wave signal or in the form of a plurality of pulses and may have any suitable electrical signal parameters for creating the cavitation. For example, the electrical signal may have an amplitude of about 500 volts (V) to about 5000 V, a pulse width of about 1 microsecond to about 200 microseconds, and a frequency of about 0.5 Hertz (Hz) to about 5 Hz.

In some examples, after the initial cavitation procedure, stent 22 may be optionally repositioned at target treatment site 62 within fluid 68 (156) and using energy source 28, deliver an additional electrical signal between primary electrode 24 and secondary electrode 26 through fluid 68 to cause fluid 68 to undergo cavitation (158). For example, after the initial round of cavitation, catheter 30 may be repositioned relative to valve 60 to provide treatment to another portion of calcified lesion 64. Additionally, or alternatively, stent 22 may be collapsed and redeployed as part of the repositioning. For example, from the partially expanded configuration, outer elongated member 42 of catheter 30 may be advanced distal relative to inner elongated member 40 such that outer elongated member 42 forces stent 22 into the collapsed configuration between inner and outer elongated members 40 and 42. Distal end 32B of elongated member 32 may then be repositioned relative to target treatment site 62 within fluid 68 to address another part of calcified lesion 64. Outer elongated member 42 may then be partially retracted relative to inner elongated member 40 such that distal end 42B of outer elongated member 42 is positioned proximal to distal end 22B of stent 22 and distal to proximal end 22A. Distal end 22B of stent 22 may re-expand to the partially expanded configuration followed by deliver, using energy source 28, an additional electrical signal between primary electrode 24 and secondary electrode 26 to cause fluid 68 to undergo further cavitation.

In some examples, the techniques of FIG. 10 may also include deploying a filter device (not shown) downstream of target treatment site 62 (e.g., downstream of stent 22) and collecting emboli with the filter device during the cavitation procedure. The deployment of the filter device and collection of emboli from the blood stream of a patient may be performed using any suitable techniques or devices. In some examples, the filter device may be incorporated with catheter 30 or the filter device may be deployed using a catheter other than catheter 30.

After completion of the cavitation procedure using catheter 30, outer elongated member 42 may be retracted relative to inner elongated member 40 such that distal end 42B of outer elongated member 42 is positioned proximal to proximal end 22A of stent 22 and stent 22 may be deployed in its expanded configuration at target treatment site 62.

Catheter 30 and/or other components of the medical assembly may then be removed from the patient.

Various examples have been described. These and other examples are within the scope of the following claims.

What is claimed is:

1. A method comprising:

electrically coupling a stent to an energy source, wherein the stent comprises a primary electrode, wherein the stent is configured to expand from a collapsed configuration to an expanded configuration;

electrically coupling a secondary electrode to the energy source;

wherein the secondary electrode is carried by a catheter comprising an inner elongated member comprising the secondary electrode, and an outer elongated member configured to be retracted relative to the inner elongated member, wherein the stent is configured to be positioned between the inner and outer elongated members;

retracting the outer elongated member relative to the inner elongated member such that a distal end of the outer elongated member is proximal to a distal end of the stent and distal to a proximal end of the stent, wherein retracting the outer elongated member comprises expanding the distal end of the stent to a partially expanded configuration within the fluid, wherein while in the partially expanded configuration the primary electrode is configured to be electrically coupled to the energy source via the catheter; and delivering, using the energy source, an electrical signal between the primary electrode and the secondary electrode through a fluid in contact with the primary electrode to cause the fluid to undergo cavitation to generate a pressure pulse wave within the fluid while the stent is in the partially expanded configuration.

2. The method of claim 1, further comprising:

collapsing the stent to the collapsed configuration;

repositioning the catheter within the fluid;

re-expanding the stent to the partially expanded configuration; and delivering, using the energy source, an additional electrical signal between the primary electrode and the secondary electrode, wherein delivery of the additional electrical signal causes the fluid to undergo cavitation that results in the generation of a pressure pulse wave within the fluid.

3. The method of claim 1, wherein collapsing the stent to the collapsed configuration comprises advancing the outer elongated member distal relative to the inner elongated member such the outer elongated member forces the stent into the collapsed configuration.

4. The method of claim 1, further comprising:

retracting the outer elongated member relative to the inner elongated member such that the distal end of the outer elongated member is proximal to the proximal end of the stent;

deploying the stent in the expanded configuration within the fluid; and removing the catheter from the fluid.

5. The method of claim 4, wherein deploying the stent in the expanded configuration within the fluid comprises deploying the stent adjacent a native heart valve.

6. The method of claim 1, wherein delivering the electrical signal comprises delivering, using the energy source, a plurality of electrical pulses having a pulse width of between about 1 microsecond (μs) and about 200 μs.

7. The method of claim 1, wherein the step of delivering the electrical signal includes delivering an electrical signal in the form of at least one of a corona, electrical arc, and a spark.

8. The method of claim 1, further comprising:

directing the stent through vasculature of a patient to a target treatment site containing a calcified lesion prior to the step of delivering the electrical signal.

9. The method of claim 8, wherein the step of delivering the electrical signal includes the pressure pulse wave disrupting the calcified lesion.

10. The method of claim 9, wherein the step of disrupting the calcified lesion includes the stent not in contact with the calcified lesion.

11. The method of claim 9, further comprising:

implanting the stent within the patient following the step of disrupting the calcified lesion.

12. The method of claim 8, wherein the target treatment site is within the vasculature of the patient.

13. The method of claim 8, wherein the target treatment site is a native heart valve.

14. The method of claim 8, wherein the fluid includes blood flowing within the patient.

15. The method of claim 1, further comprising:

deploying an embolic protection device downstream of the stent prior to the step of delivering the electrical signal.

16. The method of claim 15, further comprising:

directing the pressure pulse wave at a calcified lesion to disrupt the calcified lesion; and collecting portions of the calcified lesion dislodged by the pressure pulse wave within the embolic protection device.

17. A method comprising:

electrically coupling a stent to an energy source, wherein the stent comprises a primary electrode, wherein the stent is configured to expand from a collapsed configuration to an expanded configuration;

electrically coupling a secondary electrode to the energy source;

directing the stent through vasculature of a patient to a target treatment site containing a calcified lesion; and following the step of directing, delivering, using the energy source, an electrical signal between the primary electrode and the secondary electrode through a fluid in contact with the primary electrode to cause the fluid to undergo cavitation to generate a pressure pulse wave within the fluid;

wherein the step of delivering the electrical signal includes the pressure pulse wave disrupting the calcified lesion while the stent is not in contact with the calcified lesion.

18. A method comprising:

electrically coupling a stent to an energy source, wherein the stent comprises a primary electrode, wherein the stent is configured to expand from a collapsed configuration to an expanded configuration;

electrically coupling a secondary electrode to the energy source;

directing the stent through vasculature of a patient to a target treatment site containing a calcified lesion; and following the step of directing, delivering, using the energy source, an electrical signal between the primary electrode and the secondary electrode through a fluid in contact with the primary electrode to cause the fluid to undergo cavitation to generate a pressure pulse wave within the fluid;

wherein the target treatment site is a native heart valve.

19. The method of claim 18, wherein the step of delivering the electrical signal includes the pressure pulse wave disrupting the calcified lesion.

20. The method of claim 18, wherein the calcified lesion is at least one of calcium buildup on the native heart valve, calcium buildup adjacent the native heart valve, and calcium buildup within the native heart valve.

* * * * *